(12) United States Patent
Washburn et al.

(10) Patent No.: US 7,816,395 B2
(45) Date of Patent: *Oct. 19, 2010

(54) PYRROLIDINONE ANILINES AS PROGESTERONE RECEPTOR MODULATORS

(75) Inventors: David G. Washburn, King of Prussia, PA (US); Tram H. Hoang, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 579 days.

This patent is subject to a terminal disclaimer.

(21) Appl. No.: 11/834,709

(22) Filed: Aug. 7, 2007

(65) Prior Publication Data

US 2008/0039517 A1    Feb. 14, 2008

Related U.S. Application Data

(60) Provisional application No. 60/821,841, filed on Aug. 9, 2006.

(51) Int. Cl.
*A61K 31/4015* (2006.01)
*C07D 207/04* (2006.01)
(52) U.S. Cl. .................. 514/424; 548/543; 548/550
(58) Field of Classification Search ................ 548/541, 548/543, 550; 514/424
See application file for complete search history.

(56) References Cited

U.S. PATENT DOCUMENTS

2008/0194536 A1    8/2008    Jones et al.

FOREIGN PATENT DOCUMENTS

| WO | WO-92/22527 A2 | 12/1992 |
| WO | WO 2005/085185 | 9/2005 |
| WO | WO-2006/113552 A2 | 10/2006 |
| WO | WO2007/065093 | 6/2007 |
| WO | WO-2007/065093 A2 | 6/2007 |
| WO | WO2008/077089 | 6/2008 |

*Primary Examiner*—Golam M Shameem
(74) *Attorney, Agent, or Firm*—Robert H. Brink

(57) ABSTRACT

The present invention relates to a compound represented by the following formula:

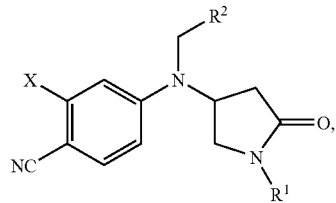

or a pharmaceutically acceptable salt thereof, or a solvate thereof, or a combination thereof, wherein $R^1$, $R^2$, and X are as defined herein. Compounds of the present invention are useful as progesterone receptor modulators.

5 Claims, No Drawings

PYRROLIDINONE ANILINES AS PROGESTERONE RECEPTOR MODULATORS

CROSS-REFERENCE TO PREVIOUS APPLICATION

This application claims the benefit of U.S. provisional 60/821,841 filed 9 Aug. 2006.

BACKGROUND OF THE INVENTION

The present invention relates to pyrrolidinone anilines that are useful as progesterone receptor modulators.

Endometriosis is a disease characterized by the growth of endometrial tissue (called lesions) at extrauterine sites. This lesion attachment can result in pain, dysmenorrhea, dyspareunia, and infertility. It is estimated that greater than 80% of patients presenting with chronic pelvic pain are eventually diagnosed with endometriosis. The prevalence of the disease is about 7-10% of women of reproductive years with a familial association risk increase of 10-fold. Definitive diagnosis is only reached by laparoscopy, but typically there is about a ten year delay from disease onset to conclusive diagnosis. Consistent with their uterine origins, it is believed that the endometriotic lesions are hormonally dependent upon estrogen; consequently, therapies that functionally antagonize estrogen production or action, such as drugs containing progesterone receptor (PR) modulators, are efficacious in alleviating symptoms. Current therapeutic goals include reducing pain with anti-inflammatory agents and suspending the ovarian cycle using hormonal modulation drugs.

Another disease believed to be hormonally responsive to estrogen is uterine leiomyomas (fibroids), which appear as benign uterine smooth muscle tumors occurring primarily in women of reproductive age. Fibroids occur at rates of 20-25% and are the leading indication for hysterectomies. The most common symptoms are menorrhagia, pelvic pain/discomfort, bladder and bowel compression symptoms, and possibly infertility. Medical treatments for leiomyomas consist of those commonly prescribed for endometriosis, with treatments containing progesterone receptor modulators being most common due to safety, tolerability, ease of use and cost.

Most drug development has focused on modulation by full agonism or antagonism of progesterone receptors. For example, progestins are molecules that interact with progesterone receptor to activate or repress gene expression in target cells in a manner presumed to be progesterone-like. Though progestins are used in oral contraception, hormone therapy, and treatment of reproductive disorders, such as endometriosis and leiomyomas, these agents cause a number of adverse effects, including breakthrough bleeding, mood altering, acne, weight gain, and breast tenderness. Paradoxically, progesterone receptor antagonists such as mifepristone have been suggested as potential therapies, but the data are limited with few patients and no placebo-controlled randomized trials.

D. DeManno et al. (*Steroids* 68 (2003) 1019-1032), report that asoprisnil is a progesterone receptor modulator with mixed agonist/antagonistic activities. While the efficacy of the agent in treatment of endometriosis or fibroids is uncertain, early data from healthy female subjects indicate that the agent induces endometrial atrophy and amenorrhea, which suggests a predominantly progesterone receptor antagonist action in humans. Unfortunately, PR antagonists such as RU-486 tend to be abortifacient.

Accordingly, it would be desirable to discover a way to suppress estrogen-dependent endometriotic growth while reducing the systemic effects associated with current progesterone receptor modulating therapy.

SUMMARY OF THE INVENTION

In a first aspect, the present invention provides a compound represented by the following formula:

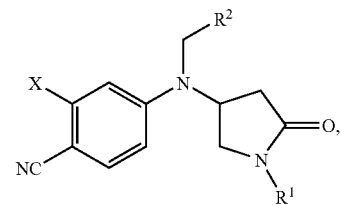

or a pharmaceutically acceptable salt thereof,
where X is H, halo, or $CF_3$;
$R^1$ is H, $C_1$-$C_6$-alkyl, $C_1$-$C_6$-alkoxycarbonyl-$(CH_2)_o$—, $C_1$-$C_6$-alkylcarbonyloxy-$(CH_2)_p$—, $C_1$-$C_6$-alkoxy-$C_1$-$C_5$-alkyl, hydroxy-$C_1$-$C_6$-alkyl, $C_3$-$C_6$-cycloalkyl, heterocycloalkyl-$(CH_2)_m$—, $C_1$-$C_6$-alkyl-heterocycloalkyl-$(CH_2)_m$—, —$CH_2CF_3$, $C_1$-$C_6$-alkylcarbonyl-$(CH_2)_o$—, $C_3$-$C_4$-alkenyl, naphthyl, —$(CH_2)_m$-heteroaryl-$(R^3)_n$, or —$(CH_2)_m$-phenyl-$(R^{3'})_n$; and
$R^2$ is $C_1$-$C_5$-alkyl, $C_1$-$C_6$-alkoxycarbonyl, $C_1$-$C_6$-alkoxycarbonyl-$C_1$-$C_5$-alkyl, $C_1$-$C_6$-alkoxy-$C_1$-$C_5$-alkyl, $C_3$-$C_6$-cycloalkyl, $C_3$-$C_6$-cycloalkenyl, heterocycloalkyl, $C_1$-$C_6$-alkyl-heterocycloalkyl, $C_2$-$C_4$-alkenyl, naphthyl, heteroaryl-$(R^3)_n$, or phenyl-$(R^{3'})_n$;
where m is an integer from 0 to 6; n is an integer from 0 to 5; o is an integer from 1 to 6; p is an integer from 2 to 6; where each $R^3$ is independently $C_1$-$C_6$-alkyl, F, Cl, Br, $CF_3$, $C_1$-$C_6$-alkoxy, dimethylamino, $C_2$-$C_4$-alkenyl, or CN, or where 2 of the $R^3$ groups, together with the heteroaryl ring to which they are attached form a fused ring; and where each $R^{3'}$ is independently $C_1$-$C_6$-alkyl, F, Cl, Br, $CF_3$, $C_1$-$C_6$-alkoxy, dimethylamino, $C_2$-$C_4$-alkenyl, or CN, or where 2 of the $R^{3'}$ groups, together with the phenyl ring to which they are attached form a fused bicyclic ring.

Compounds of the present invention are useful as progesterone receptor modulators.

DETAILED DESCRIPTION OF THE INVENTION

The present invention is a compound represented by the following formula:

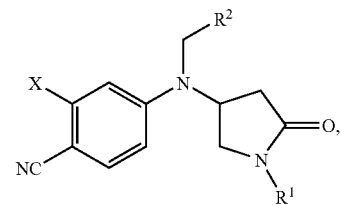

or a pharmaceutically acceptable salt thereof;
where X is H, halo, or $CF_3$;
$R^1$ is H, $C_1$-$C_6$-alkyl, $C_1$-$C_6$-alkoxycarbonyl-$(CH_2)_o$—, $C_1$-$C_6$-alkylcarbonyloxy-$(CH_2)_p$—, $C_1$-$C_6$-alkoxy-$C_1$-$C_5$- alkyl, hydroxy-$C_1$-$C_6$-alkyl, $C_3$-$C_6$-cycloalkyl, heterocycloalkyl-$(CH_2)_m$—, $C_1$-$C_6$-alkyl-heterocycloalkyl-$(CH_2)_m$—, —$CH_2CF_3$, $C_1$-$C_6$-alkylcarbonyl-$(CH_2)_o$—, $C_3$-$C_4$-alkenyl, naphthyl, —$(CH_2)_m$-heteroaryl-$(R^3)_n$, or —$(CH_2)_m$-phenyl-$(R^3)_n$; and $R^2$ is $C_1$-$C_5$-alkyl, $C_1$-$C_6$-alkoxycarbonyl, $C_1$-$C_6$-alkoxycarbonyl-$C_1$-$C_5$-alkyl, $C_1$-$C_6$-alkoxy-$C_1$-$C_5$-alkyl, $C_3$-$C_6$-cycloalkyl, $C_3$-$C_6$-cycloalkenyl, heterocycloalkyl, $C_1$-$C_6$-alkyl-heterocycloalkyl, $C_2$-$C_4$-alkenyl, naphthyl, -heteroaryl-$(R^3)_n$, or -phenyl-$(R^3)_n$;

where m is an integer from 0 to 6; n is an integer from 0 to 5; o is an integer from 1 to 6; p is an integer from 2 to 6; where each $R^3$ is independently $C_1$-$C_6$-alkyl, F, Cl, Br, $CF_3$, $C_1$-$C_6$-alkoxy, dimethylamino, $C_2$-$C_4$-alkenyl, or CN, or where 2 of the $R^3$ groups, together with the heteroaryl ring to which they are attached form a fused ring; and where each $R^{3'}$ is independently $C_1$-$C_6$-alkyl, F, Cl, Br, $CF_3$, $C_1$-$C_6$-alkoxy, dimethylamino, $C_2$-$C_4$-alkenyl, or CN, or where 2 of the $R^{3'}$ groups, together with the phenyl ring to which they are attached form a fused bicyclic ring.

As used herein, "$C_{1-6}$-alkyl" refers to a straight or branched chain radical of 1 to 6 carbon atoms, including, methyl, ethyl, n-propyl, isopropyl, n-butyl, isobutyl, t-butyl, n-pentyl, isopentyl, neopentyl, and n-hexyl and isomers thereof.

Examples of suitable $C_1$-$C_6$-alkoxy groups include methoxy and ethoxy groups; examples of suitable $C_1$-$C_6$-alkoxycarbonyl-$(CH_2)_o$— groups include —$C(CH_3)_2C(O)OCH_2CH_3$ and —$CH_2CH_2C(O)O$— t-butyl groups; an example of a suitable $C_1$-$C_6$-alkoxy-$C_1$-$C_6$-alkyl group is $CH_3OCH_2$— (methoxymethyl); examples of $C_1$-$C_6$-alkylcarbonyloxy-$(CH_2)_p$ groups include $CH_3CH_2C(O)OCH_2CH_2$— and $CH_3C(O)OCH_2CH_2$—; examples of suitable $C_3$-$C_6$-cycloalkyl groups include cyclopentyl and cyclohexyl groups; an example of a suitable $C_3$-$C_6$-cycloalkenyl group is cyclohenenyl.

As used herein, "heterocycloalkyl" refers to a 3-6-membered ring that contains at least one heteroatom selected from N, O, and S. Examples of suitable heterocycloalkyl groups include piperidinyl, pyrrolidinyl, pyrazinyl, morpholino, and 1,3-dioxolan-2-yl groups. Similarly, "$C_1$-$C_6$-alkyl-heterocycloalkyl" refers to a heterocycloalkyl group substituted with a $C_1$-$C_6$-alkyl group. An example of a $C_1$-$C_6$-alkyl-heterocycloalkyl group is N-methylpiperidinyl. Similarly, an example of a heterocycloalkyl-$(CH_2)_m$—, group is piperidinyl-$CH_2$—, and an example of a $C_1$-$C_6$-alkyl-heterocycloalkyl-$(CH_2)_m$— group is $CH_3$-piperidinyl-$CH_2$—.

The term "heteroaryl" is used herein to describe an aromatic group that contains at least one heteroatom selected from N, O, and S. Examples of suitable heteroaryl groups include pyridinyl, furyl, thienyl, imidazolyl, pyrrolyl, pyrazolyl, oxazolyl, isoxazolyl, thiazolyl, isothiazolyl, triazolyl, tetrazolyl, pyrimidinyl, and benzothiadiazolyl groups. The heteroaryl and phenyl groups may also be substituted as described herein. Heteroaryl also includes more than one heteroaryl groups, for example, pyridinylthienyl and methoxypyridinylthienyl groups.

$C_{3-4}$-alkenyl refers to allyl, isopropenyl, —$CH_2CH$=$CHCH_3$, and —$CH_2CH_2CH$=$CH_2$ groups.

When $R^2$ is heteroaryl-$(R^3)_n$ or phenyl-$(R^{3'})$ and n is 2 or 3, two of the $R^3$ or $R^{3'}$ groups can, together with the heteroaryl or phenyl groups respectively to which they are attached, form a fused group. Examples of such fused bicyclic groups include benzodioxinyl and benzodioxolyl groups.

The term "$IC_{50}$" is used herein to refer to the molar concentration of a compound required to inhibit binding of 50% of Fluormone PL Red to the progesterone receptor. Furthermore, $pIC_{50}$ is the negative log of the molar $IC_{50}$.

Pharmaceutically acceptable salts of the compounds of the present invention include salts formed by the addition of an inorganic acid such as hydrochloric acid, hydrobromic acid, sulfuric acid, nitric acid, or phosphoric acid; or by the addition of an organic acid such as acetic acid, fumaric acid, succinic acid, maleic acid, citric acid, benzoic acid, p-toluenesulfonic acid, methanesulfonic acid, naphthalenesulfonic acid, or tartaric acid.

The compounds of the present invention may exist as optical isomers including diastereoisomers and enantiomers, and mixtures of isomers in all ratios including racemic mixtures. Indeed, another aspect of the present invention is a compound of the formula:

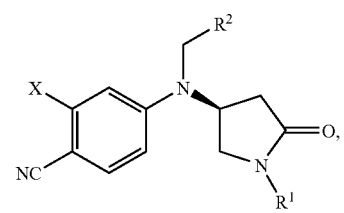

or a pharmaceutically acceptable salt thereof, where $R^1$, $R^2$, and X are as previously defined.

In another aspect, wherein $R^1$ is $C_1$-$C_6$-alkyl or benzyl; $R^2$ is phenyl-$(R^3)_n$, where n is an integer from 0 to 2; and X is chloro.

In another aspect $R^1$ is methyl, ethyl, or isopropyl; $R^{3'}$ is chloro, fluoro, trifluoromethyl, or methyl; and n=0, 1, 2, or 3.

In yet another aspect, the present invention is a compound represented by the following structure:

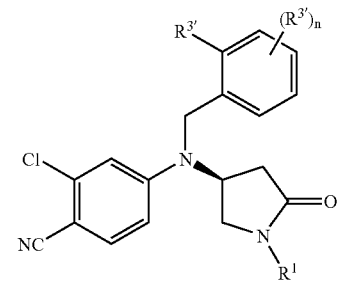

or a pharmaceutically acceptable salt thereof, where n is 0, 1, or 2.

In another aspect, the present invention is a compound or a pharmaceutically acceptable salt thereof, wherein the compound is selected from the group consisting of:

2-chloro-4-{[(3S)-1-methyl-5-oxo-3-pyrrolidinyl][(2-methylphenyl)methyl]amino}benzonitrile;

2-chloro-4-{[(2-fluorophenyl)methyl][(3S)-1-methyl-5-oxo-3-pyrrolidinyl]amino}benzonitrile;

2-chloro-4-{[(2,4-difluorophenyl)methyl][(3S)-1-ethyl-5-oxo-3-pyrrolidinyl]amino}benzonitrile;

2-chloro-4-{[(2,3-difluorophenyl)methyl][(3S)-1-methyl-5-oxo-3-pyrrolidinyl]amino}benzonitrile;

2-chloro-4-[[(3S)-1-ethyl-5-oxo-3-pyrrolidinyl](phenylmethyl)amino]benzonitrile;

2-chloro-4-{[(2,5-dichlorophenyl)methyl][(3S)-1-ethyl-5-oxo-3-pyrrolidinyl]amino}benzonitrile;

2-chloro-4-{[(2-chloro-5-fluorophenyl)methyl][(3S)-1-ethyl-5-oxo-3-pyrrolidinyl]amino}benzonitrile;

2-chloro-4-{[(2-chlorophenyl)methyl][(3S)-1-ethyl-5-oxo-3-pyrrolidinyl]amino}benzonitrile;
2-chloro-4-{[(3S)-1-ethyl-5-oxo-3-pyrrolidinyl][(2-methylphenyl)methyl]amino}benzonitrile;
2-chloro-4-{[(2,3-difluoro-4-methylphenyl)methyl][(3S)-1-ethyl-5-oxo-3-pyrrolidinyl]amino}benzonitrile;
2-chloro-4-{[(3S)-1-ethyl-5-oxo-3-pyrrolidinyl][(5-fluoro-2-methylphenyl)methyl]amino}benzonitrile;
2-chloro-4-{[(2-chlorophenyl)methyl][(3S)-1-(1-methylethyl)-5-oxo-3-pyrrolidinyl]amino}benzonitrile; and
2-chloro-4-{[(2,5-dichlorophenyl)methyl][(3S)-1-(1-methylethyl)-5-oxo-3-pyrrolidinyl]amino}benzonitrile.

The present invention also relates to a pharmaceutical composition comprising the compound of the formula of the present invention and a pharmaceutically acceptable carrier therefor. The composition may be formulated for administration by any route, such as oral, topical or parenteral. The compositions may be in the form of tablets, capsules, powders, granules, lozenges, creams or liquid preparations, such as oral or sterile parenteral solutions or suspensions.

Biological Assays
Abbreviations:
HATU—O-(7-Azabenzotriazol-1-yl)-N,N,N',N'-tetramethyluronium hexafluorophosphate
DMA—N,N-Dimethylacetamide
NMM—N-Methylmorpholine
NMO—N-Methylmorpholine oxide
HMDS—Hexamethyldisilazane
CDI—Carbonyl diimidazole
CBz—$C_6H_5OC(O)$—

Acquest/Biosystems is a multi-mode reader (FP reader); CHAPS refers to 3-cholamidopropyl-dimethylammonio1-propanesulfonate; DTT refers to dithiothreitol.

PR Binding Assay—The assay was performed according to the manufacturers protocol (PR Competitor Assay Kit, Red—(Invitrogen, Carlsbad, Calif.—Product No. P2962)) with minor amendments. Briefly, 40 nM PR-Ligand Binding Domain, 2 nM Fluormone PL Red and 1 mM DTT were dissolved and mixed in Complete PR RED Buffer supplemented with 2 mM CHAPS. 10 µL of the mix was dispensed to each well of Greiner low volume plates, containing compounds at the required concentration. The plates were spun for 1 min at 200 g, covered to protect the reagents from light, and then incubated at room temperature for approximately 2 hours. Plates were read on an Acquest™ Ultra High Throughput Screening Assay detection system (trademark of LJL Biosystems, Sunnyvale, Calif.) using a 530-25 nm excitation and 580-10 nm emission interference filter and a 561 nm Dichroic mirror.

Data Analysis
All data was normalized to the mean of 16 high and 16 low control wells on each plate. A four parameter curve fit of the following form was then applied $$y = \frac{a-d}{1+(x/c)^b} + d$$

Where a is the minimum, b is the Hill slope, c is the XC50 and d is the maximum. Data is presented as the mean $pIC_{50}$ with the standard deviation of the mean of n experiments.

Methods of Use
The compounds of the present invention may be useful in the treatment of disease or condition associated with endometreosis, uterine fibroids, dysmenorrhea, menorrhagia, pre-term labor, and infertility. The compounds may also be useful as contraceptives or for hormone therapy.

Accordingly, the present invention further relates to a method of treating a patient comprising administering to the patient an effective amount of a compound of formula I or a pharmaceutically-acceptable salt thereof, or a solvate thereof or combination thereof to treat endometreosis or uterine fibroids.

Compound Preparation
The compounds of the present invention can be prepared in a variety of ways. For example, in a first method, amino acid 1a can be converted to the amide 1b (Scheme 1). Treatment of 1b with $P_2S_5$ yields the desired thioamide 1c. Selective reduction of the thioamide 1c leads to the corresponding secondary amine which upon reflux in toluene cyclizes to the pyrrolidinone 1d. Acidic cleavage of the Boc-amine 1d yields the primary amine 1e which then can undergo an aryl fluoride displacement to form the aniline 1f. Subsequent treatment of 1f with NaH and an electrophile ($R^2CH_2Y$, where Y is advantageously Br or I) yields the desired product 1 g.

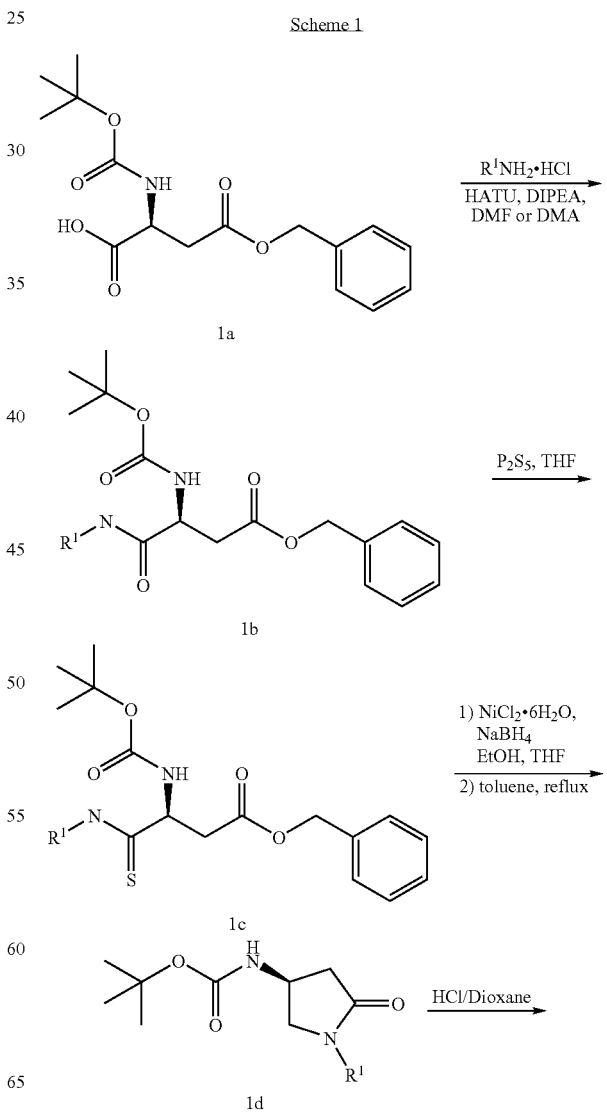

Scheme 1

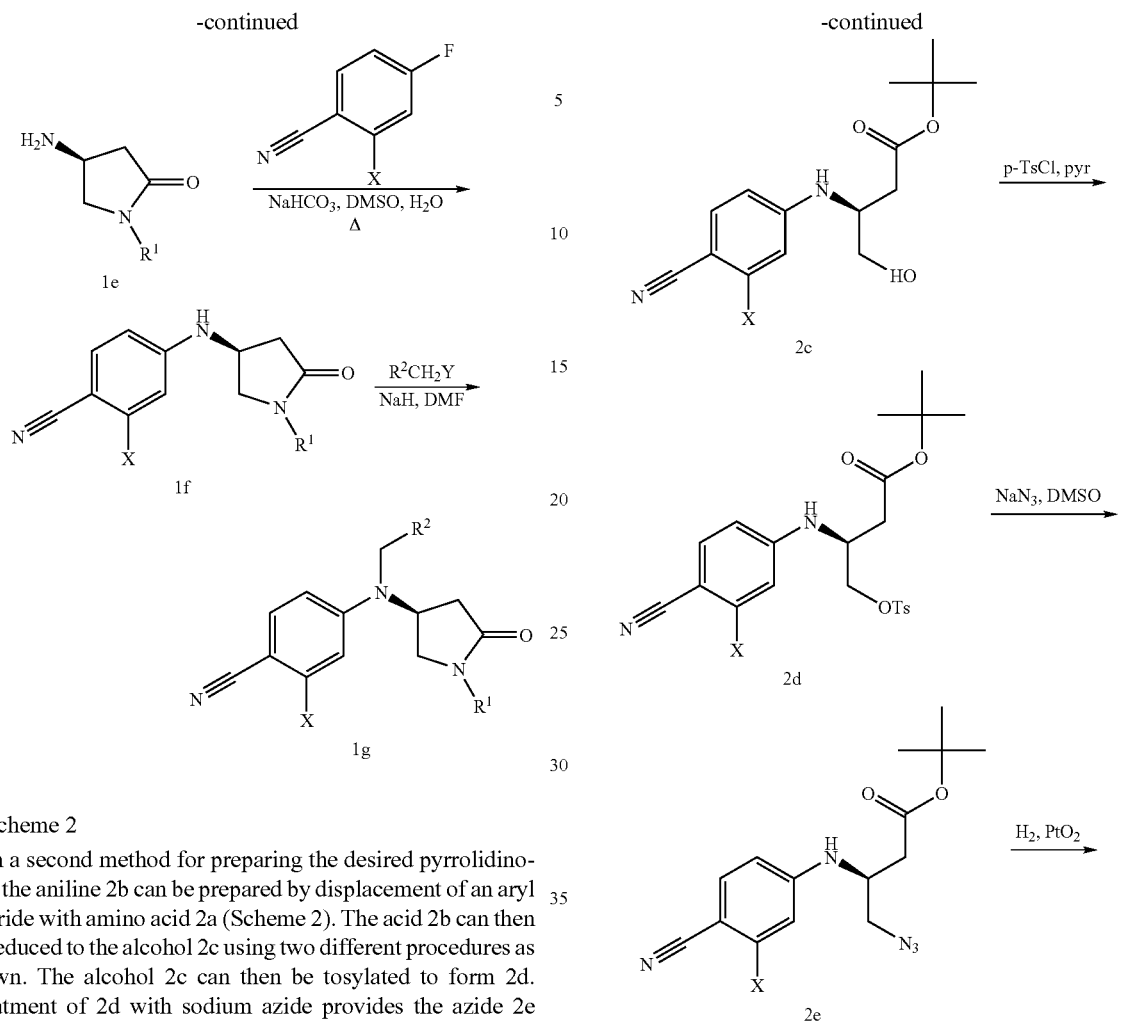

Scheme 2

In a second method for preparing the desired pyrrolidinones, the aniline 2b can be prepared by displacement of an aryl fluoride with amino acid 2a (Scheme 2). The acid 2b can then be reduced to the alcohol 2c using two different procedures as shown. The alcohol 2c can then be tosylated to form 2d. Treatment of 2d with sodium azide provides the azide 2e which can then be reduced under hydrogenation conditions to furnish the desired primary amine 2f.

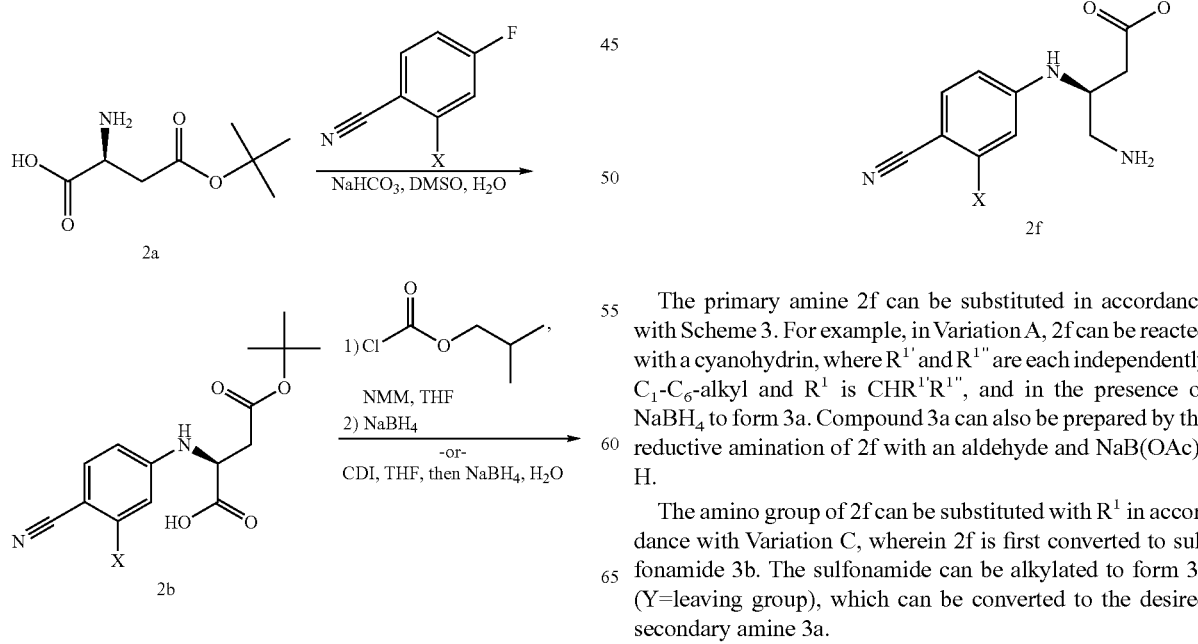

The primary amine 2f can be substituted in accordance with Scheme 3. For example, in Variation A, 2f can be reacted with a cyanohydrin, where $R^{1'}$ and $R^{1'''}$ are each independently $C_1$-$C_6$-alkyl and $R^1$ is $CHR^{1'}R^{1'''}$, and in the presence of $NaBH_4$ to form 3a. Compound 3a can also be prepared by the reductive amination of 2f with an aldehyde and $NaB(OAc)_3H$.

The amino group of 2f can be substituted with $R^1$ in accordance with Variation C, wherein 2f is first converted to sulfonamide 3b. The sulfonamide can be alkylated to form 3c (Y=leaving group), which can be converted to the desired secondary amine 3a.

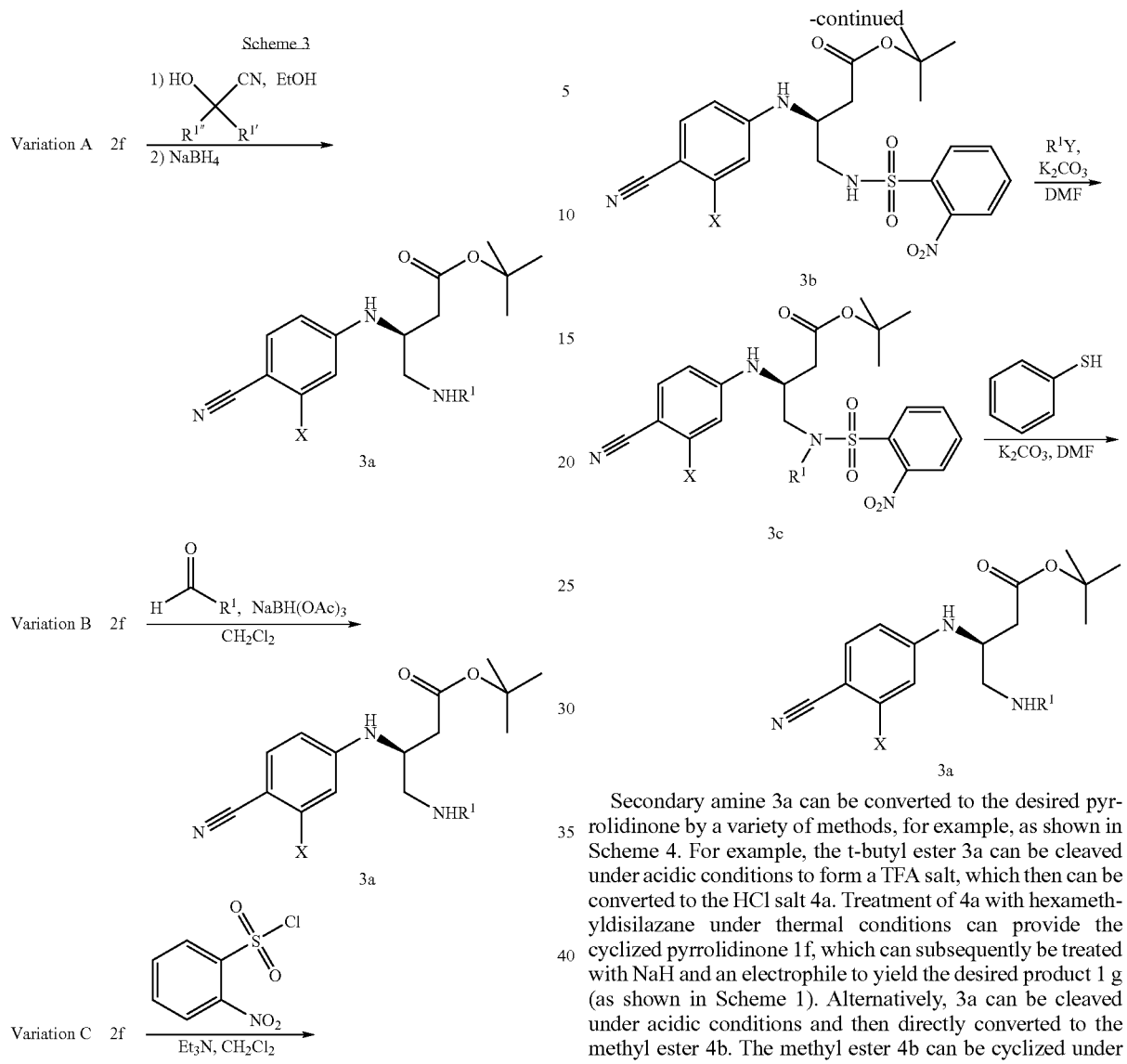

Secondary amine 3a can be converted to the desired pyrrolidinone by a variety of methods, for example, as shown in Scheme 4. For example, the t-butyl ester 3a can be cleaved under acidic conditions to form a TFA salt, which then can be converted to the HCl salt 4a. Treatment of 4a with hexamethyldisilazane under thermal conditions can provide the cyclized pyrrolidinone 1f, which can subsequently be treated with NaH and an electrophile to yield the desired product 1 g (as shown in Scheme 1). Alternatively, 3a can be cleaved under acidic conditions and then directly converted to the methyl ester 4b. The methyl ester 4b can be cyclized under different basic conditions to form 1f, which can be converted to 1 g (as shown in Scheme 1).

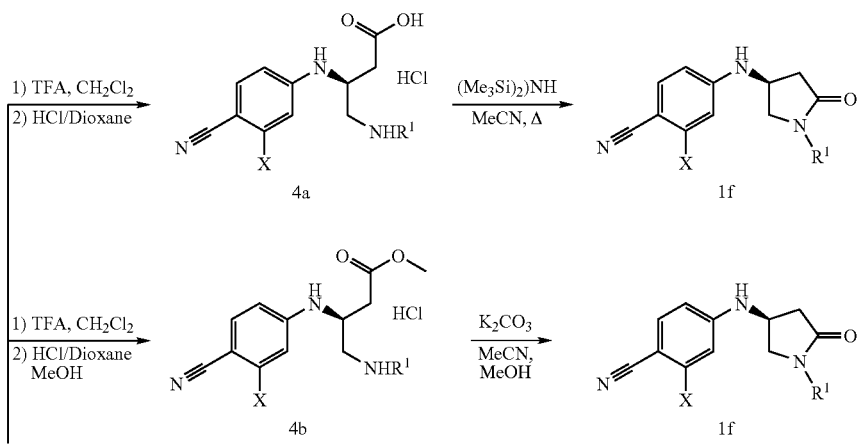

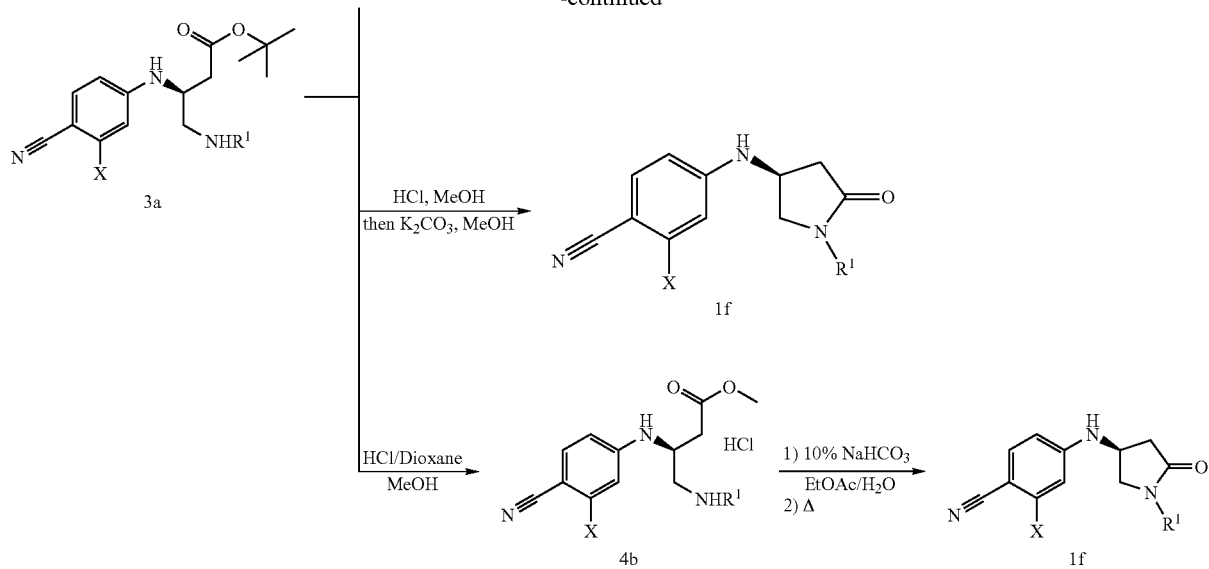
The allyl substituted pyrrolidinone 5a can be converted to the diol 5b via OsO₄ and NMO. 5b can then be cleaved to the aldehyde 5c which is directly reduced to the desired alcohol 5d. Furthermore, treatment of 5a with borane-THF yields the alcohol 5e.
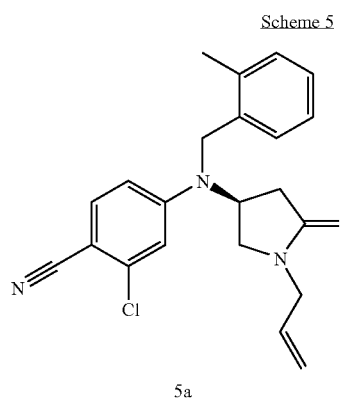
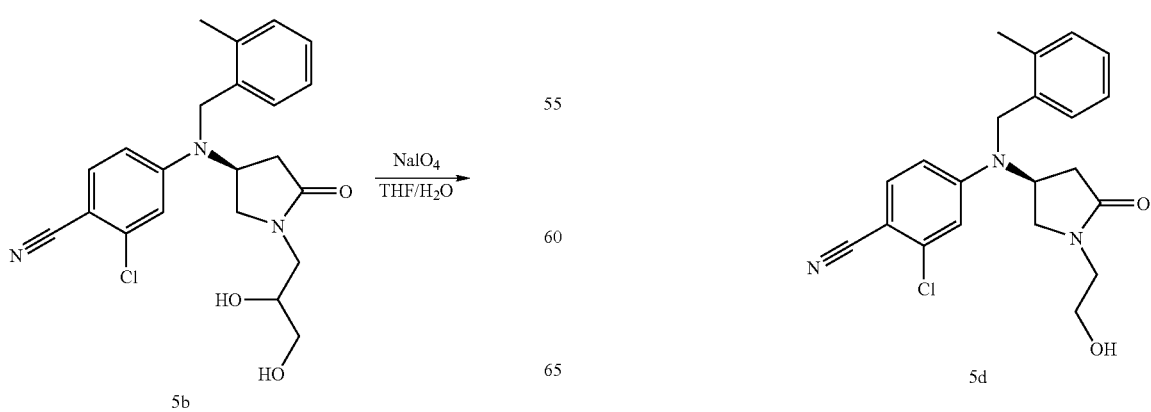

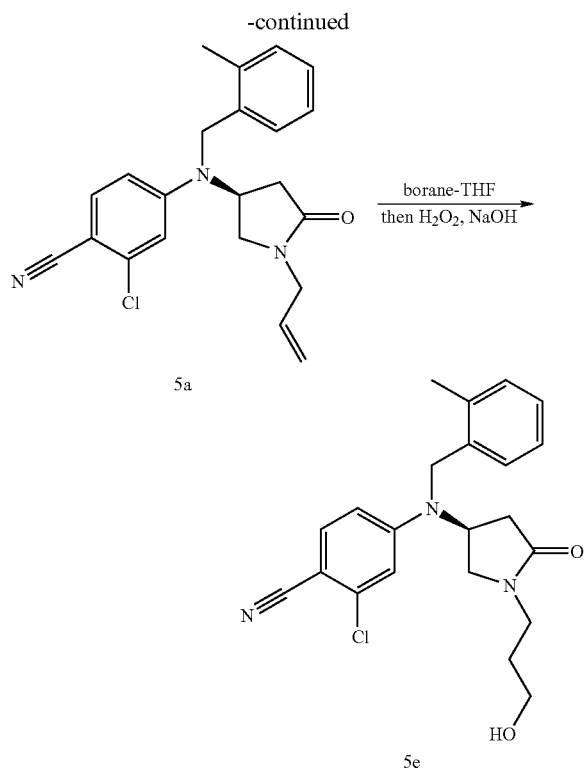

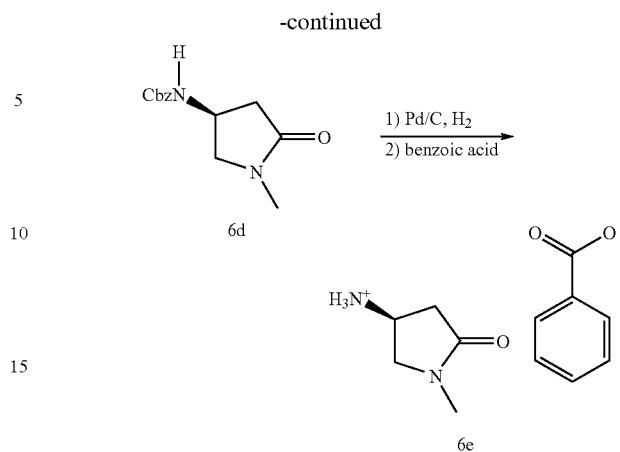

An alternative route to the pyrrolidinone core is described in Scheme 6. Aminosuccinic acid 6a can be protected with a Cbz group, then condensed to anhydride 6b. The anhydride 6b can then be converted to imide 6c by reaction with methylamine and acetic anhydride. Imide 6c can then be converted through selective reduction to pyrrolidnone 6d, which can be deprotected under hydrogenation conditions then converted to the benzoic acid salt of pyrrolidinone 6e. The pyrollidinone salt 6e can be converted to compounds of the present invention, as shown in Scheme 1.

EXPERIMENTAL

The following examples are for illustrative purposes only and are not intended to limit the scope of the invention. Using the assay described hereinabove, all of these examples exhibit an $IC_{50}$ of less than 10 μM.

Proton nuclear magnetic resonance ($^1$H NMR) spectra were recorded at 400 MHz, and chemical shifts are reported in parts per million (ppm) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. $CDCl_3$ is deuteriochloroform, DMSO-$d_6$ is hexadeuteriodimethylsulfoxide, and $CD_3OD$ or $d_4$-$CH_3OH$ is tetradeuteriomethanol. Mass spectra were obtained using electrospray (ES) or atmospheric pressure chemical ionization (APCI) techniques. E. Merck Silica Gel 60 F-254 thin layer plates were used for thin layer chromatography. Flash chromatography was carried out on E. Merck Kieselgel 60 (230-400 mesh) silica gel or on an ISCO Combiflash purification system using pre-filled silica gel cartridges. Preparative HPLC was performed using Gilson chromatography systems using a 30×100 mm Xterra Prep RP column at a flow rate of 40 mL/min. The solvent system used was a variable gradient of 18% to 90% acetonitrile/water using either 0.1% TFA or ammonium hydroxide to adjust the pH to 10. Celite® is a filter aid composed of acid-washed diatomaceous silica, and is a registered trademark of Manville Corp., Denver, Colo.

Intermediate 1

2-Chloro-4-{[(3S)-1-methyl-5-oxo-3-pyrrolidinyl]amino}benzonitrile

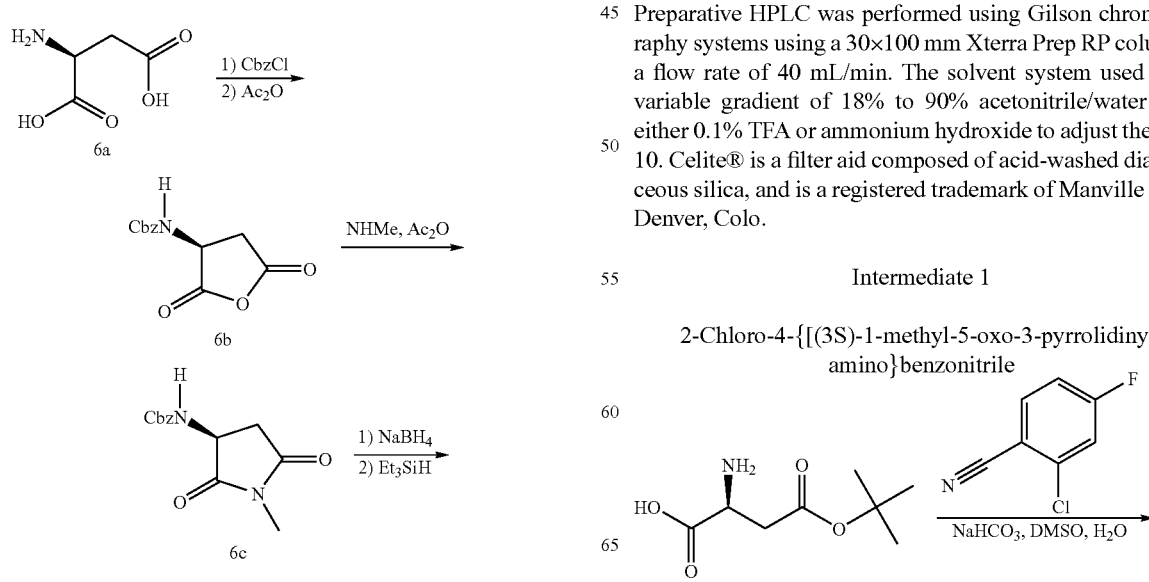

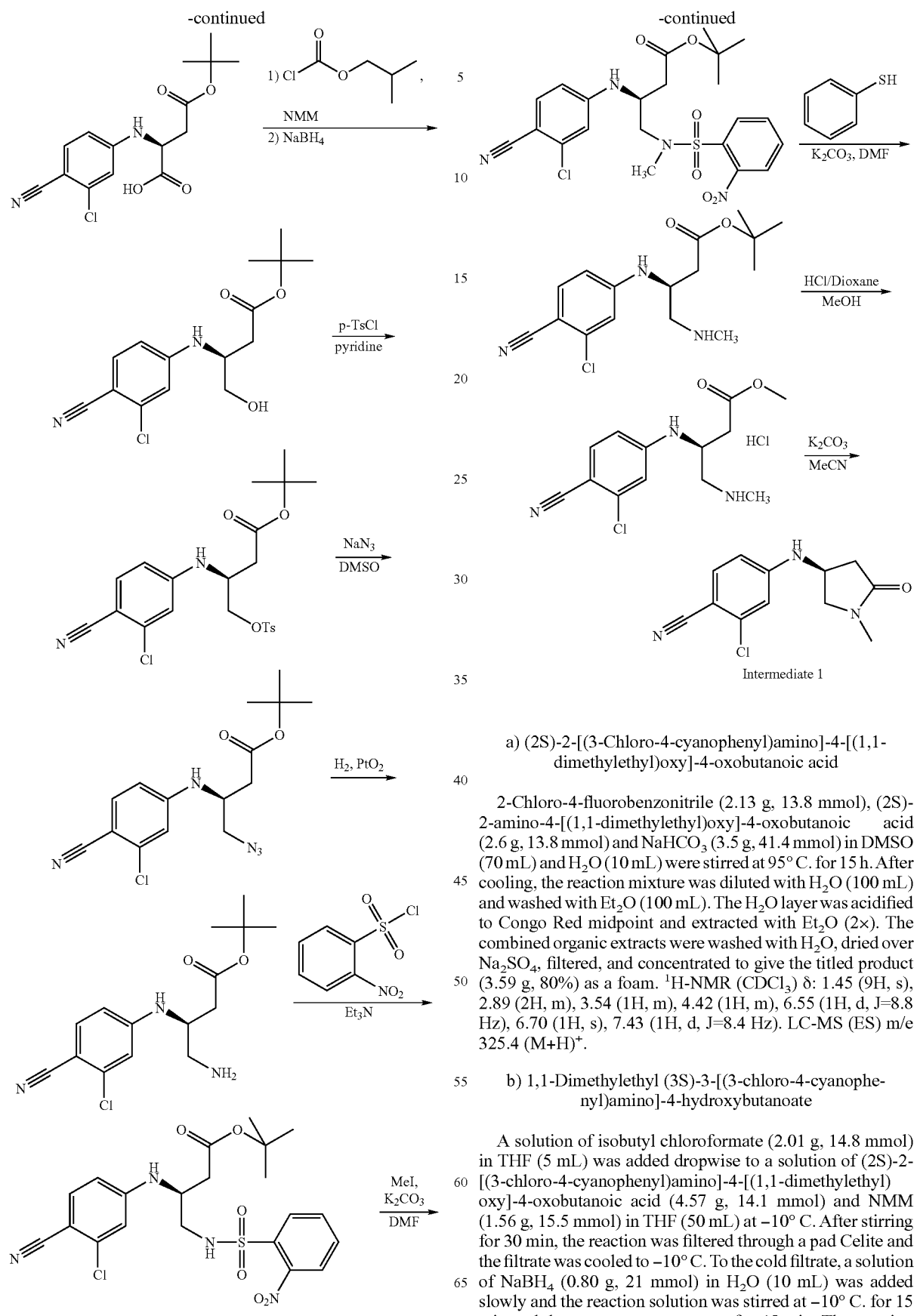

a) (2S)-2-[(3-Chloro-4-cyanophenyl)amino]-4-[(1,1-dimethylethyl)oxy]-4-oxobutanoic acid 2-Chloro-4-fluorobenzonitrile (2.13 g, 13.8 mmol), (2S)-2-amino-4-[(1,1-dimethylethyl)oxy]-4-oxobutanoic acid (2.6 g, 13.8 mmol) and NaHCO$_3$ (3.5 g, 41.4 mmol) in DMSO (70 mL) and H$_2$O (10 mL) were stirred at 95° C. for 15 h. After cooling, the reaction mixture was diluted with H$_2$O (100 mL) and washed with Et$_2$O (100 mL). The H$_2$O layer was acidified to Congo Red midpoint and extracted with Et$_2$O (2×). The combined organic extracts were washed with H$_2$O, dried over Na$_2$SO$_4$, filtered, and concentrated to give the titled product (3.59 g, 80%) as a foam. $^1$H-NMR (CDCl$_3$) δ: 1.45 (9H, s), 2.89 (2H, m), 3.54 (1H, m), 4.42 (1H, m), 6.55 (1H, d, J=8.8 Hz), 6.70 (1H, s), 7.43 (1H, d, J=8.4 Hz). LC-MS (ES) m/e 325.4 (M+H)$^+$.

b) 1,1-Dimethylethyl (3S)-3-[(3-chloro-4-cyanophenyl)amino]-4-hydroxybutanoate

A solution of isobutyl chloroformate (2.01 g, 14.8 mmol) in THF (5 mL) was added dropwise to a solution of (2S)-2-[(3-chloro-4-cyanophenyl)amino]-4-[(1,1-dimethylethyl)oxy]-4-oxobutanoic acid (4.57 g, 14.1 mmol) and NMM (1.56 g, 15.5 mmol) in THF (50 mL) at −10° C. After stirring for 30 min, the reaction was filtered through a pad Celite and the filtrate was cooled to −10° C. To the cold filtrate, a solution of NaBH$_4$ (0.80 g, 21 mmol) in H$_2$O (10 mL) was added slowly and the reaction solution was stirred at −10° C. for 15 min and then at room temperature for 45 min. The reaction was quenched with aqueous NH$_4$Cl and extracted with Et$_2$O (2×). The organic extracts were washed with 5% Na$_2$CO$_3$, cold 0.1N HCl and H$_2$O, dried over Na$_2$SO$_4$, filtered, and concentrated. The residue was purified via silica gel chromatography with 0% MeOH in CH$_2$Cl$_2$ grading to 3% MeOH in CH$_2$Cl$_2$ to afford the titled product (2.83 g, 64%) as a solid. $^1$H-NMR (CDCl$_3$) δ: 1.45 (9H, s), 2.61 (2H, m), 3.79 (2H, d, J=4.4 Hz), 3.93 (1H, m), 6.55 (1H, dd, J=8 Hz, 4 Hz), 6.72 (1H, d, J=2 Hz), 7.41 (1H, d, J=8.8 Hz). LC-MS (ES) m/e 311.5 (M+H)$^+$.

c) 1,1-Dimethylethyl (3S)-3-[(3-chloro-4-cyanophenyl)amino]-4-{[(4-methylphenyl)sulfonyl]oxy}butanoate p-Toluenesulfonyl chloride (18.2 g, 96 mmol) was added portion-wise to an ice cold solution of 1,1-dimethylethyl (3S)-3-[(3-chloro-4-cyanophenyl)amino]-4-hydroxybutanoate (27.0 g, 87 mmol) in pyridine (75 mL). After stirring at 0° C. for 15 min, ice bath was removed and the reaction was stirred at room temperature for 2.5 h. The reaction was poured into stirred, ice/H$_2$O (400 mL). When the product solidified, it was filtered, and the solid washed well with H$_2$O. The solid was dissolved in EtOAc (350 mL), and washed successively with H$_2$O, aq. citric acid, and H$_2$O. The EtOAc solution was treated with charcoal, dried (MgSO$_4$), filtered, and the solvent evaporated. The crude product was triturated with a mixture of Et$_2$O (150 mL) and petroleum ether (50 mL) to afford the pure product (35.0 g, 87%). $^1$H-NMR (CDCl$_3$) δ: 1.42 (9H, s), 2.47 (3H, s), 2.60 (2H, m), 4.04 (1H, m), 4.22 (2H, m), 6.45 (1H, dd, J=8 Hz, 4 Hz), 6.56 (1H, d, J=2.4 Hz), 7.35 (3H, m), 7.75 (2H, d, J=8.4 Hz). LC-MS (ES) m/e 465.3 (M+H)$^+$.

d) 1,1-Dimethylethyl (3S)-4-azido-3-[(3-chloro-4-cyanophenyl)amino]butanoate 1,1-Dimethylethyl (3S)-3-[(3-chloro-4-cyanophenyl)amino]-4-{[(4-methylphenyl)sulfonyl]oxy}butanoate (35.0 g, 76 mmol) and sodium azide (9.83 g, 150 mmol) in DMF (150 mL) were stirred at 65° C. for 2.25 h. After cooling, the reaction was diluted with cold H$_2$O (500 mL) and extracted with Et$_2$O (3×). The combined organic extracts were washed with H$_2$O (3×), treated with charcoal and dried (MgSO$_4$), filtered and the solvent evaporated. The residue was dissolved in a small amount of Et$_2$O and filtered through a short plug of silica gel. Evaporation of the filtrate afforded the titled compound (26.9 g, >100%) as an oil. $^1$H-NMR (CDCl$_3$) δ: 1.46 (9H, s), 2.58 (2H, m), 3.56 (2H, d, J=5.2 Hz), 3.99 (1H, m), 6.54 (1H, d, J=8 Hz), 6.99 (1H, s), 7.43 (1H, d, J=8.8 Hz). LC-MS (ES) m/e 336.3 (M+H)$^+$.

e) 1,1-Dimethylethyl (3S)-4-amino-3-[(3-chloro-4-cyanophenyl)amino]butanoate PtO$_2$ (0.98 g) in EtOH (100 mL) was reduced with H$_2$ (40 psi) on a Parr shaker for 20 minutes. To this mixture was added a solution of 1,1-dimethylethyl (3S)-4-azido-3-[(3-chloro-4-cyanophenyl)amino]butanoate (25.5 g, 76 mmol) in EtOH (100 mL) and the reaction was shaken on a Parr shaker under H$_2$ (35 psi) for 2.5 h. The reaction mixture was filtered through a pad Celite and concentrated. The residue was dissolved in CH$_2$Cl$_2$, washed with H$_2$O, dried over MgSO$_4$, filtered and the solvent removed. The residue was triturated with Et$_2$O (75 mL), chilled, and filtered to afford the titled product (19.8 g, 84%). $^1$H-NMR (CD$_3$OD) δ: 1.39 (9H, s), 2.39 (1H, m), 2.58 (1H, m), 2.73 (1H, m), 2.79 (1H, m), 3.97 (1H, m), 6.68 (1H, d, J=8 Hz), 6.84 (1H, s), 7.44 (1H, d, J=8.8 Hz). LC-MS (ES) m/e 310.6 (M+H)$^+$.

f) 1,1-Dimethylethyl (3S)-3-[(3-chloro-4-cyanophenyl)amino]-4-{[(2-nitrophenyl)sulfonyl]amino}butanoate A solution of 2-nitrobenzenesulfonyl chloride (14.15 g, 64 mmol) in CH$_2$Cl$_2$ (50 mL) was added dropwise over 20 min to an ice cold solution of 1,1-dimethylethyl (3S)-4-amino-3-[(3-chloro-4-cyanophenyl)amino]butanoate (19.8 g, 64 mmol) and Et$_3$N (6.5 g, 64 mmol) in CH$_2$Cl$_2$ (150 mL) and the reaction was stirred at room temperature for 30 min. The reaction was washed with H$_2$O and cold 0.1 N HCl. The organic layer was dried over CaCl$_2$, filtered, and concentrated. The crude product was used directly in the next step.

g) 1,1-Dimethylethyl (3S)-3-[(3-chloro-4-cyanophenyl)amino]-4-{methyl[(2-nitrophenyl)sulfonyl]amino}butanoate A mixture of the crude 1,1-dimethylethyl (3S)-3-[(3-chloro-4-cyanophenyl)amino]-4-{[(2-nitrophenyl)sulfonyl]amino}butanoate from the previous step, MeI (18.2 g, 128 mmol) and K$_2$CO$_3$ (325 mesh, 17.7 g, 128 mmol) in DMF (100 mL) was stirred at room temperature for 70 min. The reaction was diluted with H$_2$O (200 mL) and extracted with Et$_2$O (3×). The organic extracts were washed with H$_2$O (2×), dried over CaCl$_2$, filtered, and concentrated. The crude product was used directly in the next step.

h) 1,1-Dimethylethyl (3S)-3-[(3-chloro-4-cyanophenyl)amino]-4-(methylamino)butanoate The crude 1,1-dimethylethyl (3S)-3-[(3-chloro-4-cyanophenyl)amino]-4-{methyl[(2-nitrophenyl)sulfonyl]amino}butanoate from the previous step (31.8 g), phenyl hydrosulfide (1.5 equiv., 10.32 g, 94 mmol), and K$_2$CO$_3$ (325 mesh, 3 equiv., 25.9 g, 188 mmol) in DMF (100 mL) were stirred at room temperature for 30 min. The reaction mixture was diluted with H$_2$O (300 mL) and extracted with Et$_2$O (4×). The organic extracts were washed with H$_2$O, and 10% aq. Na$_2$CO$_3$, dried, and concentrated to give the titled product which contaminated with the 2-nitrophenyl phenyl sulfide by product (31.7 g). This contaminated product was used directly in the next step.

i) Methyl (3S)-3-[(3-chloro-4-cyanophenyl)amino]-4-(methylamino)butanoate, hydrochloride The 1,1-dimethylethyl (3S)-3-[(3-chloro-4-cyanophenyl)amino]-4-(methylamino)butanoate from the previous step (31.4 g) was dissolved in a mixture of MeOH (100 mL) and 4N HCl/dioxane (30 mL) and heated to 60° C. for 1.25 h. The solvents were concentrated to a slurry, Et$_2$O (200 mL) was added, the solid filtered, washed well with Et$_2$O to give the titled compound (15.6 g).

j) 2-Chloro-4-{[(3S)-1-methyl-5-oxo-3-pyrrolidinyl]amino}benzonitrile

A mixture of methyl (3S)-3-[(3-chloro-4-cyanophenyl)amino]-4-(methylamino)butanoate, hydrochloride (15.6 g., 49 mmole) and K$_2$CO$_3$ (325 mesh, 15.0 g, 110 mmole) in MeCN (120 mL) and MeOH (30 mL) was heated with stirring at 68° C. for 20 min. The solvents were evaporated, and the residue partitioned between EtOAc and H$_2$O. The aqueous layer was extracted with EtOAc (2×), the combined EtOAc extracts were washed with H$_2$O and brine, dried (MgSO$_4$) and the solvent evaporated. The crude product (10.3 g) was triturated with Et$_2$O, chilled and the solid filtered to give the titled compound (9.93 g, 81%). LC-MS (ES) m/e 250 (M+H)$^+$.

Alternative Route to Intermediate 1

2-Chloro-4-{[(3S)-1-methyl-5-oxo-3-pyrrolidinyl]amino}benzonitrile

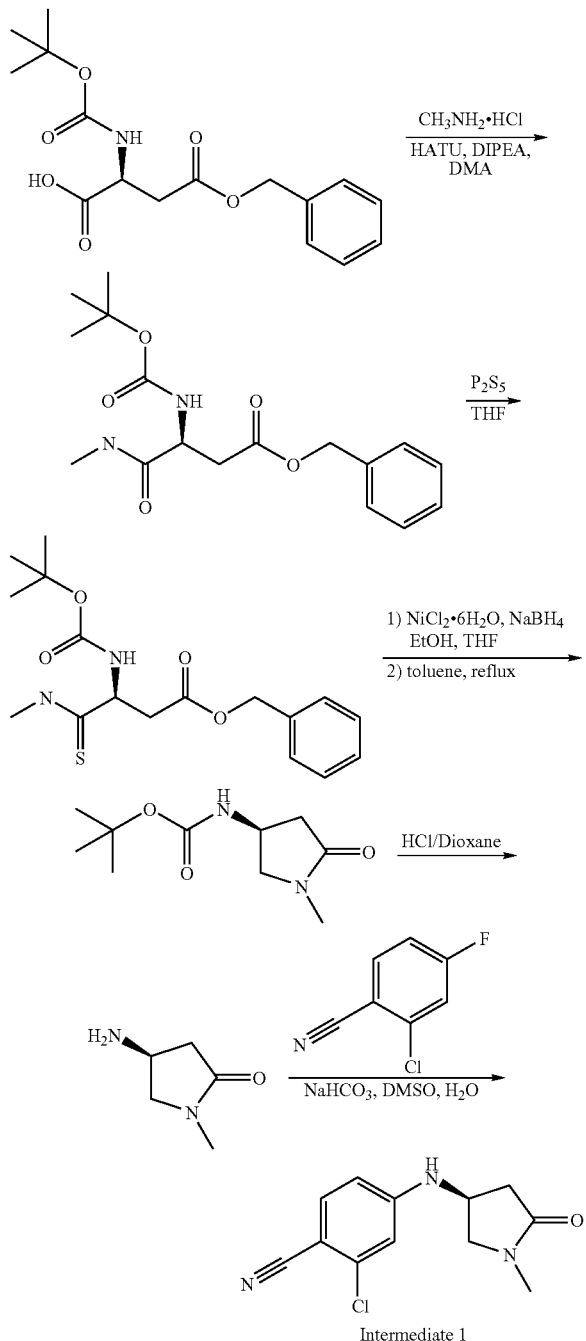

Intermediate 1 a) Phenylmethyl N$^2$-{[(1,1-dimethylethyl)oxy]carbonyl}-N$^1$-methyl-L-α-asparaginate N,N-Diisopropylethylamine (15.10 g, 116.8 mmol) and HATU (10.77 g, 28.34 mmol) were added to a suspension of Boc-Asp-(OBzl)-OH (7.61 g, 23.54 mmol) and methylamine hydrochloride (5.03 g, 74.50 mmol) in DMA (31 mL). After stirring at room temperature for 18 h, the reaction mixture was diluted with CH$_2$Cl$_2$ and washed with saturated NaHCO$_3$. The organic layer was washed with H$_2$O several times, dried over Na$_2$SO$_4$, filtered, and concentrated. The residue was purified via silica gel chromatography with 0% MeOH in CH$_2$Cl$_2$ grading to 4% MeOH in CH$_2$Cl$_2$ to afford the titled product (6.2 g, 78%) as a white solid. $^1$H-NMR (CDCl$_3$) δ: 1.471 (9H, s), 2.730 (1H, m), 2.818 (3H, d, J=4.8 Hz), 3.120 (1H, m), 4.520 (1H, s), 5.156 (2H, m), 5.660 (1H, s), 6.430 (1H, s), 7.378 (5H, m). LC-MS (ES) m/e 337.2 (M+H)$^+$.

b) Phenylmethyl (3S)-3-({[(1,1-dimethylethyl)oxy]carbonyl}amino)-4-(methylamino)-4-thioxobutanoate Phenylmethyl N$^2$-{[(1,1-dimethylethyl)oxy]carbonyl}-N$^1$-methyl-L-α-asparaginate (4.20 g, 12.48 mmol) and phosphorus pentasulfide (3.33 g, 7.49 mmol) were dissolved in THF (105 mL) and the reagents were stirred at room temperature for 4 h. Saturated NaHCO$_3$ was added and the reaction was extracted with EtOAc. The organic layer was concentrated and the residue was dissolved in CH$_2$Cl$_2$:Et$_2$O (1:1) and filtered through a well packed silica gel column to give the titled product (3.3 g, 75%) as a white solid. $^1$H-NMR (CDCl$_3$) δ: 1.461 (9H, s), 2.960 (1H, m), 3.149 (3H, d, J=5.2 Hz), 3.270 (1H, m), 4.820 (1H, s), 5.137 (2H, m), 5.770 (1H, s), 7.374 (5H, m), 8.380 (1H, s). LC-MS (ES) m/e 353.6 (M+H)$^+$.

c) 1,1-Dimethylethyl [(3S)-1-methyl-5-oxo-3-pyrrolidinyl]carbamate

NaBH$_4$ (2.7 g, 74.23 mmol) was added portionwise to an ice cold solution of phenylmethyl (3S)-3-({[(1,1-dimethylethyl)oxy]carbonyl}amino)-4-(methylamino)-4-thioxobutanoate (3.3 g, 9.36 mmol) and NiCl$_2$.6H$_2$O (5.1 g, 21.62 mmol) in THF (50 mL) and EtOH (50 mL) and the reaction mixture was stirred at room temperature for 2.5 days. The resulted black mixture was then filtered through a pad of Celite and the filtrate was concentrated. To this residue was added toluene (15 mL) and the solution was refluxed for 12 h. After cooling to room temperature, the reaction was concentrated and purified via silica gel chromatography with 0% MeOH in CH$_2$Cl$_2$ grading to 10% MeOH in CH$_2$Cl$_2$ to give the titled product (0.96 g, 48%) as a white solid. $^1$H-NMR (CDCl$_3$) δ: 1.466 (9H, s), 2.270 (1H, dd, J=16 Hz, 4 Hz), 2.770 (1H, m), 2.874 (3H, s), 3.260 (1H, dd, J=8 Hz, 4 Hz), 3.720 (1H, m), 4.310 (1H, s), 4.820 (1H, s). LC-MS (ES) m/e 215.2 (M+H)$^+$.

d) 2-Chloro-4-{[(3S)-1-methyl-5-oxo-3-pyrrolidinyl]amino}benzonitrile 1,1-Dimethylethyl [(3S)-1-methyl-5-oxo-3-pyrrolidinyl]carbamate (0.96 g, 4.5 mmol) was suspended in 4N HCl in dioxane (3 mL) and the mixture was stirred at room temperature for 12 h. Solvent was removed and the residue was dissolved in DMSO (27 mL) and H$_2$O (3 mL). To this solution, 2-chloro-4-fluorobenzonitrile (0.77 g, 4.90 mmol) and NaHCO$_3$ (1.89 g, 22.5 mmol) were added and the reaction mixture was stirred at 75° C. for 18 h. After cooling to room temperature, the reaction mixture was partitioned between H$_2$O and EtOAc and the organic layer was dried over Na$_2$SO$_4$, filtered, and concentrated. The residue was purified by silica gel chromatography with 0% MeOH in CH$_2$Cl$_2$ grading to 5% MeOH in CH$_2$Cl$_2$ to give the titled product (0.598 g, 53%) as a white solid. $^1$H-NMR (CDCl$_3$) δ: 2.350 (1H, m), 2.914 (4H, m), 3.305 (1H, m), 3.825 (1H, m), 4.200 (1H, m), 4.835 (1H, d, J=6.8 Hz), 6.492 (1H, dd, J=8.4 Hz, 2.4 Hz), 6.626 (1H, d, J=2.4 Hz), 7.454 (1H, d, J=8.4 Hz). LC-MS (ES) m/e 250.0 (M+H)$^+$.

Intermediate 2

-Chloro-4-{[(3S)-1-(1-methylethyl)-5-oxo-3-pyrrolidinyl]amino}benzonitrile

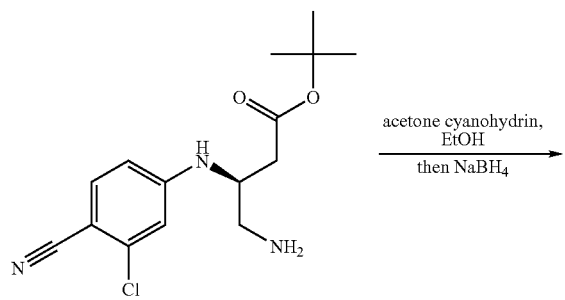

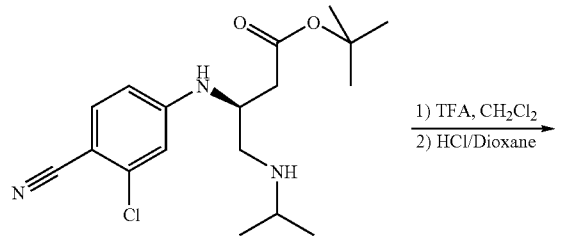

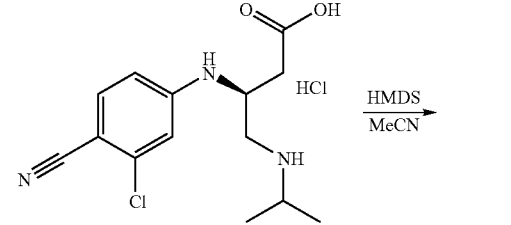

Intermediate 2 a) 1,1-Dimethylethyl (3S)-3-[(3-chloro-4-cyanophenyl)amino]-4-[(1-methylethyl)amino]butanoate A mixture of 1,1-dimethylethyl (3S)-4-amino-3-[(3-chloro-4-cyanophenyl)amino]butanoate (0.309 g, 1 mmol), acetone cyanohydrin (0.1 g, 1.18 mmol) and crushed 4 Å molecular sieves in EtOH (5 mL) was stirred at 60° C. for 6 h. After cooled down, the reaction mixture was filtered. The filtrate was treated with NaBH$_4$ (excess amount) and stirred for 2.5 h. The reaction was diluted with H$_2$O and extracted with Et$_2$O (2×). The organic extracts were washed with H$_2$O (2×), dried over Na$_2$SO$_4$, filtered, and concentrated to yield the titled product (0.33 g, 94%). LC-MS (ES) m/e 352.5 (M+H)$^+$.

b) (3S)-3-[(3-chloro-4-cyanophenyl)amino]-4-[(1-methylethyl)amino]butanoic acid hydrochloride A solution of 1,1-dimethylethyl (3S)-3-[(3-chloro-4-cyanophenyl)amino]-4-[(1-methylethyl)amino]butanoate (0.33 g, 0.94 mmol) in CH$_2$Cl$_2$ (2 mL) was treated with TFA (1 mL) for 1.5 h and the reaction was evaporated thoroughly. The residue was treated with 4N HCl in dioxane (4 mL) and then concentrated (this step was done twice) and the crude product was used directly in the next step.

c) 2-Chloro-4-{[(3S)-1-(1-methylethyl)-5-oxo-3-pyrrolidinyl]amino}benzonitrile

The crude (3S)-3-[(3-chloro-4-cyanophenyl)amino]-4-[(1-methylethyl)amino]butanoic acid hydrochloride was dissolved in MeCN (20 mL) and treated with HMDS (4 mL) and the reaction was stirred at 60° C. for 15 h. After cooled down, the reaction was diluted with H$_2$O and extracted with Et$_2$O (2×). The combined organic extracts were washed with H$_2$O (2×), dried over Na$_2$SO$_4$, filtered, concentrated, and purified by silica gel chromatography with 25% EtOAC in hexane grading to 100% EtOAc in hexane to yield the titled product (0.13 g, 49%). LC-MS (ES) m/e 277.9 (M+H)$^+$.

Intermediate 3

2-chloro-4-{[(3S)-1-ethyl-5-oxo-3-pyrrolidinyl]amino}benzonitrile

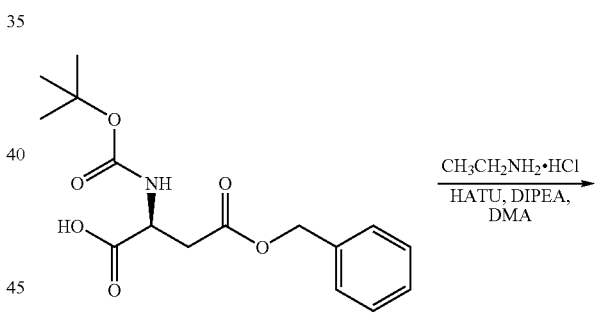

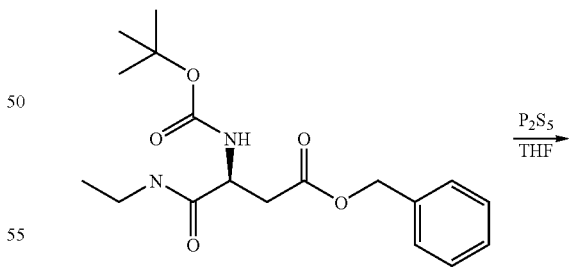

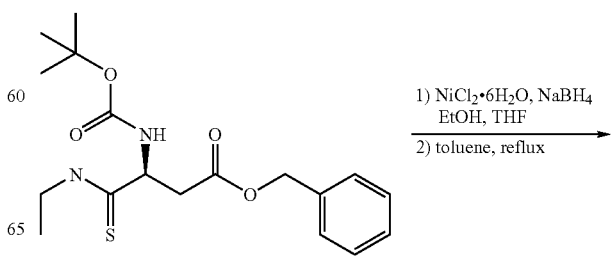

-continued

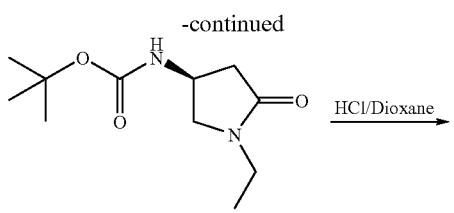

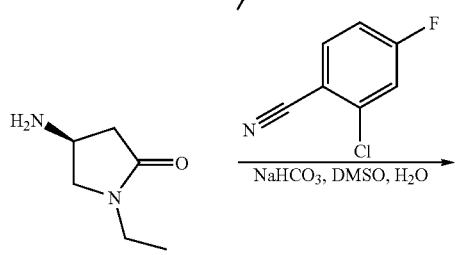

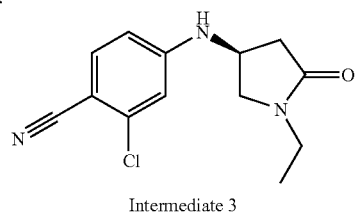

Intermediate 3 a) Phenylmethyl $N^2$-{[(1,1-dimethylethyl)oxy]carbonyl}-$N^1$-ethyl-L-α-asparaginate This compound was made according to the general procedure for the alternative route to Intermediate 1 (part a) except substituting ethylamine hydrochloride for methylamine hydrochloride. LC-MS (ES) m/e 351.4 (M+H)$^+$.

b) Phenylmethyl (3S)-3-({[(1,1-dimethylethyl)oxy]carbonyl}amino)-4-(ethylamino)-4-thioxobutanoate This compound was made according to the general procedure for the alternative route to Intermediate 1 (part b) except substituting phenylmethyl $N^2$-{[(1,1-dimethylethyl)oxy]carbonyl}-$N^1$-ethyl-L-α-asparaginate for phenylmethyl $N^2$-{[(1,1-dimethylethyl)oxy]carbonyl}-$N^1$-methyl-L-α-asparaginate. LC-MS (ES) m/e 311.2 (M−56)$^+$.

c) 1,1-Dimethylethyl [(3S)-1-ethyl-5-oxo-3-pyrrolidinyl]carbamate

This compound was made according to the general procedure for the alternative route to Intermediate 1 (part c) except substituting phenylmethyl (3S)-3-({[(1,1-dimethylethyl)oxy]carbonyl}amino)-4-(ethylamino)-4-thioxobutanoate for phenylmethyl (3S)-3-({[(1,1-dimethylethyl)oxy]carbonyl}amino)-4-(methylamino)-4-thioxobutanoate. LC-MS (ES) m/e 229.4 (M+H)$^+$.

d) 2-Chloro-4-{[(3S)-1-ethyl-5-oxo-3-pyrrolidinyl]amino}benzonitrile

This compound was made according to the general procedure for the alternative route to Intermediate 1 (part d) except substituting 1,1-dimethylethyl [(3S)-1-ethyl-5-oxo-3-pyrrolidinyl]carbamate for 1,1-dimethylethyl [(3S)-1-methyl-5-oxo-3-pyrrolidinyl]carbamate. LC-MS (ES) m/e 264.0 (M+H)$^+$.

Alternative Route to Intermediate 3

2-chloro-4-{[(3S)-1-ethyl-5-oxo-3-pyrrolidinyl]amino}benzonitrile

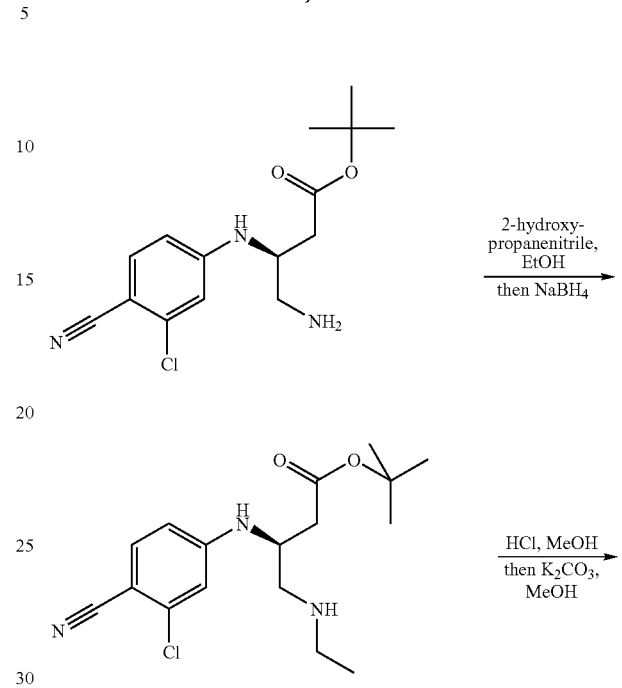

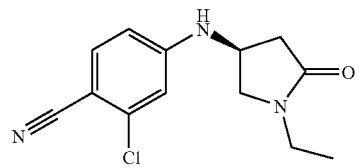

(a) 1,1-Dimethylethyl (3S)-3-[(3-chloro-4-cyanophenyl)amino]-4-(ethylamino)butanoate This compound was made using a procedure similar to Intermediate 2 (part a) except substituting 2-hydroxypropanenitrile for acetone cyanohydrin. LC-MS (ES) m/e 337.9 (M+H)$^+$.

b) 2-chloro-4-{[(3S)-1-ethyl-5-oxo-3-pyrrolidinyl]amino}benzonitrile

A solution of 1,1-dimethylethyl (3S)-3-[(3-chloro-4-cyanophenyl)amino]-4-(ethylamino)butanoate (5.66 g, 16.8 mmol), HCl (4M in dioxane, 40 mL) and MeOH (100 mL) was stirred at 65° C. for 2 h. After cooling, the reaction was concentrated. To the residue, $K_2CO_3$ (325 mesh, 6.6 g, 47.5 mmol) and MeOH (150 mL) were added and the reaction was stirred at 65° C. for 1 h. Solvent was removed and the residue was partitioned between EtOAc and $H_2O$. The organic layer was dried over $MgSO_4$ and concentrated to give the product as a white solid (2.4 g, 54%). LC-MS (ES) m/e 264.4 (M+H)$^+$.

Alternative Route to Intermediate 3

2-chloro-4-{[(3S)-1-ethyl-5-oxo-3-pyrrolidinyl]amino}benzonitrile

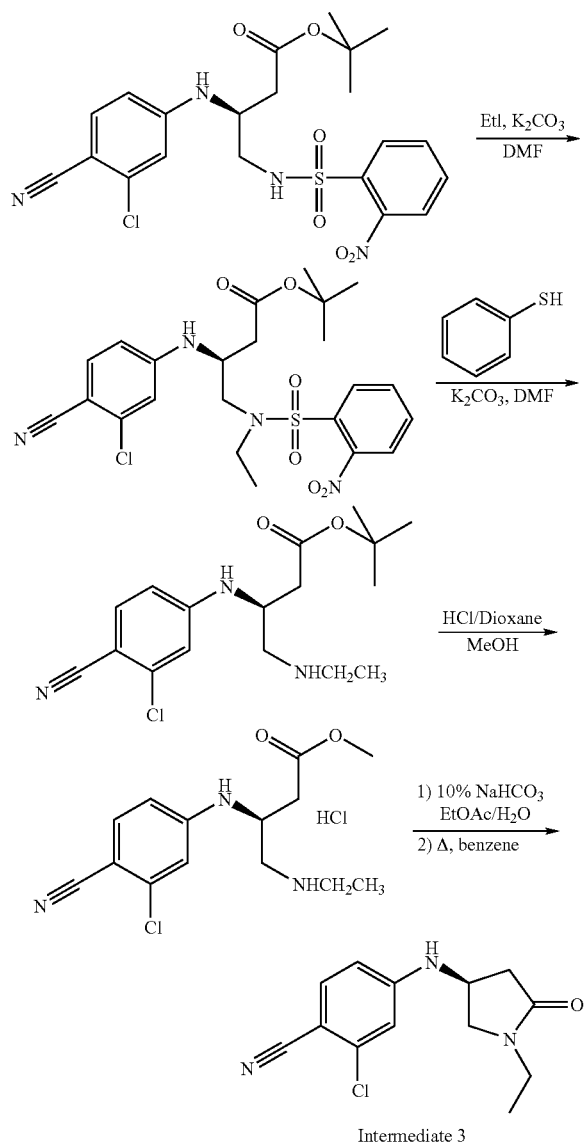

Intermediate 3 a) 1,1-Dimethylethyl (3S)-3-[(3-chloro-4-cyanophenyl)amino]-4-{ethyl[(2-nitrophenyl)sulfonyl]amino}butanoate A mixture of the crude 1,1-dimethylethyl (3S)-3-[(3-chloro-4-cyanophenyl)amino]-4-{[(2-nitrophenyl)sulfonyl]amino}butanoate from the previous step, ethyl iodide (2.59 mL, 32.4 mmol) and $K_2CO_3$ (325 mesh, 6.71 g, 48.6 mmol) in DMF (93 mL) was stirred at room temperature for 60 min. The reaction was diluted with $H_2O$ (200 mL) and extracted with $Et_2O$ (3×). The organic extracts were washed with $H_2O$ (2×), dried over $Na_2SO_4$, filtered, and concentrated. The crude product was used directly in the next step.

b) 1,1-Dimethylethyl (3S)-3-[(3-chloro-4-cyanophenyl)amino]-4-(ethylamino)butanoate The crude 1,1-dimethylethyl (3S)-3-[(3-chloro-4-cyanophenyl)amino]-4-{ethyl[(2-nitrophenyl)sulfonyl]amino}butanoate from the previous step (16.2 mmol), phenyl hydrosulfide (1.0 equiv., 1.78 g, 16.2 mmol), and $K_2CO_3$ (325 mesh, 3 equiv., 6.71 g, 48.6 mmol) in DMF (60 mL) were stirred at room temperature for 90 min. The reaction mixture was diluted with $H_2O$ (200 mL) and extracted with $Et_2O$ (3×). The organic extracts were washed with $H_2O$, and 10% aq. $Na_2CO_3$, dried, and concentrated to give the titled product which was contaminated with the 2-nitrophenyl phenyl sulfide by-product. This contaminated product was used directly in the next step.

c) Methyl (3S)-3-[(3-chloro-4-cyanophenyl)amino]-4-(ethylamino)butanoate, hydrochloride The 1,1-dimethylethyl (3S)-3-[(3-chloro-4-cyanophenyl)amino]-4-(ethylamino)butanoate from the previous step was dissolved in a mixture of MeOH (150 mL) and 4N HCl/dioxane (20 mL) and heated to 60° C. for 3 h. The solvents were concentrated to a slurry, $Et_2O$ (200 mL) was added, the solid filtered, washed well with $Et_2O$ to give the titled compound (4.0 g).

d) 2-Chloro-4-{[(3S)-1-ethyl-5-oxo-3-pyrrolidinyl]amino}benzonitrile

Methyl (3S)-3-[(3-chloro-4-cyanophenyl)amino]-4-(ethylamino)butanoate, hydrochloride (4.0 g., 13.5 mmole) was redissolved in ethyl acetate (50 mL). Water was added (50 mL) and 10% sodium bicarbonate was added with stirring to bring the pH to 8.5. The organic layer was concentrated and redissolved in benzene (120 mL). The solution was heated with stirring at 75° C. for 6 h. The solvent was evaporated. The crude product was triturated with $Et_2O$, chilled and the solid filtered to give the titled compound (3.0 g, 84%). LC-MS (ES) m/e 263 $(M+H)^+$.

Intermediate 4

2-Chloro-4-{[(3S)-5-oxo-1-(phenylmethyl)-3-pyrrolidinyl]amino}benzonitrile

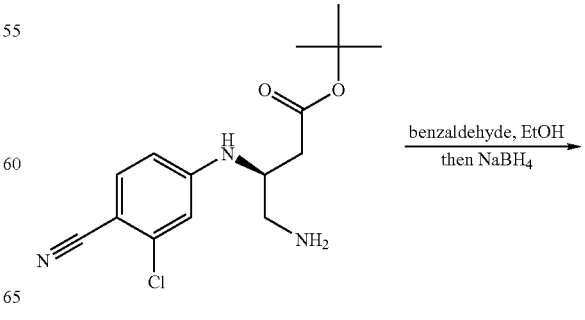

acid hydrochloride for (3S)-3-[(3-chloro-4-cyanophenyl)amino]-4-[(1-methylethyl)amino]butanoic acid hydrochloride. LC-MS (ES) m/e 326.6 (M+H)⁺.

Intermediate 5

2-chloro-4-{[(3S)-1-(2,2-dimethylpropyl)-5-oxo-3-pyrrolidinyl]amino}benzonitrile

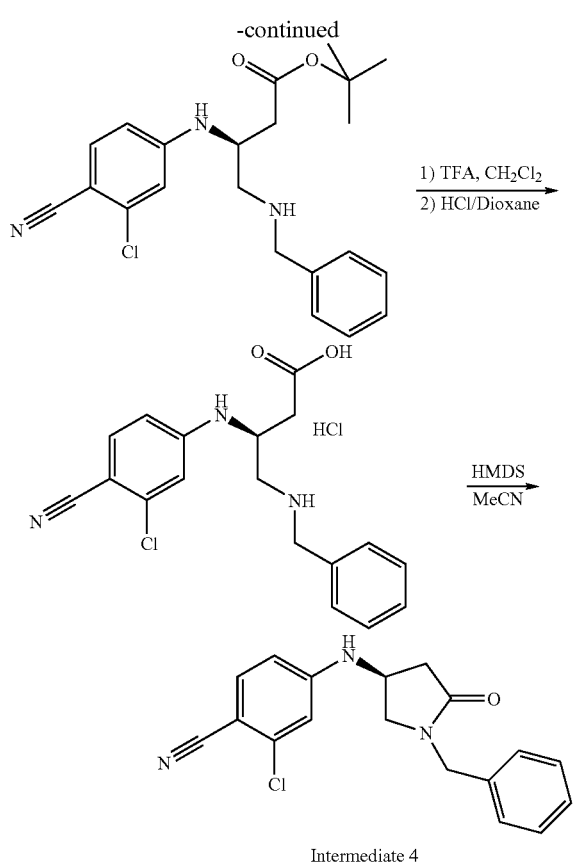

Intermediate 4 a) 1,1-Dimethylethyl (3S)-3-[(3-chloro-4-cyanophenyl)amino]-4-[(phenylmethyl)amino]butanoate 1,1-Dimethylethyl (3S)-4-amino-3-[(3-chloro-4-cyanophenyl)amino]butanoate (0.355 g, 1.15 mmol), benzaldehyde (0.12 g, 1.15 mmol), and 4 Å molecular sieves in EtOH (4 mL) were stirred at room temperature for 3 h. To this mixture, NaBH$_4$ (excess amount) was added and the reaction was stirred for additional 1 h. The reaction was filtered. The filtrate was diluted with H$_2$O and extracted with Et$_2$O (2×). The organic extracts were washed with H$_2$O, dried over Na$_2$SO$_4$, filtered, concentrated, and purified via silica gel chromatography with 0% MeOH in CH$_2$Cl$_2$ grading to 5% MeOH in CH$_2$Cl$_2$ to yield the titled product (0.27 g, 59%) as a white solid. LC-MS (ES) m/e 400.3 (M+H)⁺.

b) (3S)-3-[(3-chloro-4-cyanophenyl)amino]-4-[(phenylmethyl)amino]butanoic acid hydrochloride This compound was made using a procedure similar to Intermediate 2 (part b) except substituting 1,1-dimethylethyl (3S)-3-[(3-chloro-4-cyanophenyl)amino]-4-[(phenylmethyl)amino]butanoate for 1,1-dimethylethyl (3S)-3-[(3-chloro-4-cyanophenyl)amino]-4-[(1-methylethyl)amino]butanoate.

c) 2-Chloro-4-{[(3S)-5-oxo-1-(phenylmethyl)-3-pyrrolidinyl]amino}benzonitrile This compound was made using a procedure similar to Intermediate 2 (part c) except substituting (3S)-3-[(3-chloro-4-cyanophenyl)amino]-4-[(phenylmethyl)amino]butanoic acid hydrochloride for (3S)-3-[(3-chloro-4-cyanophenyl)amino]-4-[(1-methylethyl)amino]butanoic acid hydrochloride. LC-MS (ES) m/e 326.6 (M+H)⁺.

a) 1,1-Dimethylethyl (3S)-3-[(3-chloro-4-cyanophenyl)amino]-4-[(2,2-dimethylpropyl)amino]butanoate NaBH(OAc)$_3$ (0.5 g, 2.32 mmol) was added to a solution of 1,1-dimethylethyl (3S)-4-amino-3-[(3-chloro-4-cyanophenyl)amino]butanoate (0.48 g, 1.55 mol), and trimethylacetaldehyde (0.14 g, 1.60 mmol) in CH$_2$Cl$_2$ (35 mL). After stirring at room temperature for 2 h, the reaction was diluted with CH$_2$Cl$_2$ (35 mL), washed with saturated NaHCO$_3$, dried over Na$_2$SO$_4$, filtered, and concentrated to yield the titled product (0.575 g, 98%) as an oil. LC-MS (ES) m/e 380.6 (M+H)⁺.

b) (3S)-3-[(3-chloro-4-cyanophenyl)amino]-4-[(2,2-dimethylpropyl)amino]butanoic acid hydrochloride This compound was made using a procedure similar to Intermediate 2 (part b) except substituting 1,1-dimethylethyl (3S)-3-[(3-chloro-4-cyanophenyl)amino]-4-[(2,2-dimethylpropyl)amino]butanoate for 1,1-dimethylethyl (3S)-3-[(3-chloro-4-cyanophenyl)amino]-4-[(1-methylethyl)amino]butanoate.

c) 2-Chloro-4-{[(3S)-1-(2,2-dimethylpropyl)-5-oxo-3-pyrrolidinyl]amino}benzonitrile This compound was made using a procedure similar to Intermediate 2 (part c) except substituting (3S)-3-[(3-chloro-4-cyanophenyl)amino]-4-[(2,2-dimethylpropyl)amino]butanoic acid hydrochloride for (3S)-3-[(3-chloro-4-cyanophenyl)amino]-4-[(1-methylethyl)amino]butanoic acid hydrochloride. LC-MS (ES) m/e 306 (M+H)$^+$.

Intermediate 6

2-chloro-4-{[(3S)-1-(1-methylpropyl)-5-oxo-3-pyrrolidinyl]amino}benzonitrile a) 1,1-Dimethylethyl (3S)-3-[(3-chloro-4-cyanophenyl)amino]-4-[(1-methylpropyl)amino]butanoate This compound was made according to Intermediate 5 (part a) except substituting 2-butanone for trimethylacetaldehyde and 1,2-dichloroethane for CH$_2$Cl$_2$. LC-MS (ES) m/e 366.6 (M+H)$^+$.

b) Methyl (3S)-3-[(3-chloro-4-cyanophenyl)amino]-4-[(1-methylpropyl)amino]butanoate hydrochloride This compound was made using a procedure similar to Intermediate 1 (part i) except substituting 1,1-dimethylethyl (3S)-3-[(3-chloro-4-cyanophenyl)amino]-4-[(1-methylpropyl)amino]butanoate for 1,1-dimethylethyl (3S)-3-[(3-chloro-4-cyanophenyl)amino]-4-(methylamino)butanoate. LC-MS (ES) m/e 323.9 (M+H)$^+$.

c) 2-Chloro-4-{[(3S)-1-(1-methylpropyl)-5-oxo-3-pyrrolidinyl]amino}benzonitrile

This compound was made using a procedure similar to Intermediate 1 (part j) except substituting methyl (3S)-3-[(3-chloro-4-cyanophenyl)amino]-4-[(1-methylpropyl)amino] butanoate hydrochloride for methyl (3S)-3-[(3-chloro-4-cyanophenyl)amino]-4-(methylamino)butanoate, hydrochloride and the reaction was stirred for 6 h. LC-MS (ES) m/e 291.9 (M+H)$^+$.

Intermediate 7

2-chloro-4-{[(3S)-1-(1-ethylpropyl)-5-oxo-3-pyrrolidinyl]amino}benzonitrile

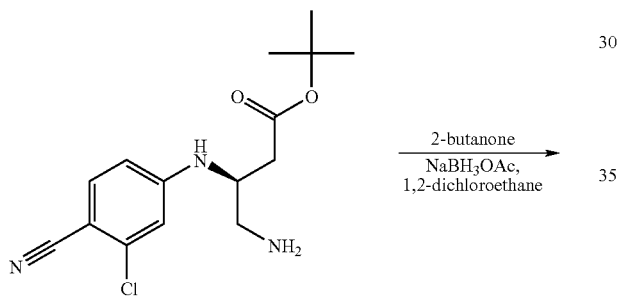

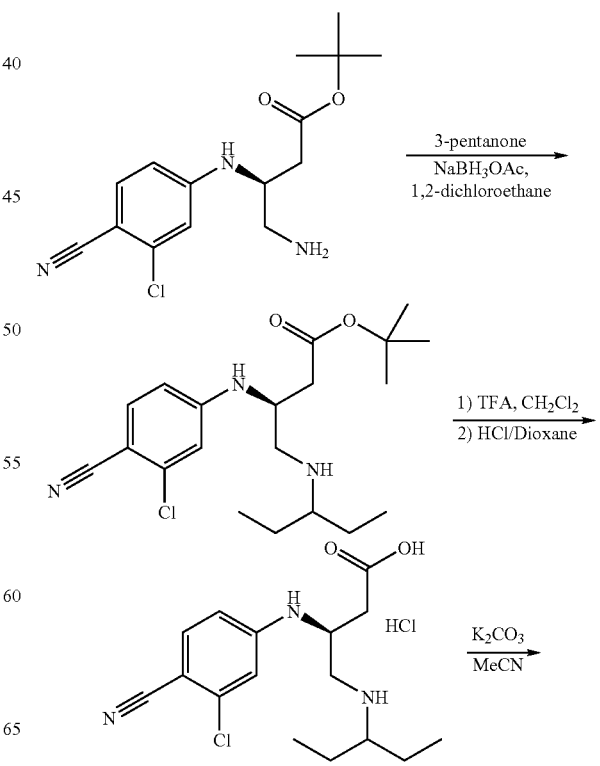

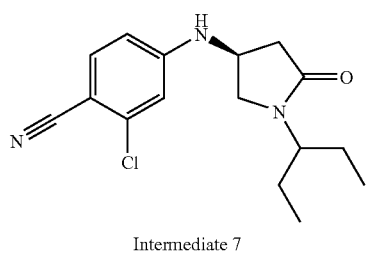

Intermediate 7 a) 1,1-Dimethylethyl (3S)-3-[(3-chloro-4-cyanophenyl)amino]-4-[(1-ethylpropyl)amino]butanoate This compound was made using a procedure similar to Intermediate 5 (part a) except substituting 3-pentanone for trimethylacetaldehyde and 1,2-dichloroethane for $CH_2Cl_2$. LC-MS (ES) m/e 380.6 (M+H)+.

b) Methyl (3S)-3-[(3-chloro-4-cyanophenyl)amino]-4-[(1-ethylpropyl)amino]butanoate hydrochloride This compound was made using a procedure similar to Intermediate 1 (part i) except substituting 1,1-dimethylethyl (3S)-3-[(3-chloro-4-cyanophenyl)amino]-4-[(1-ethylpropyl)amino]butanoate for 1,1-dimethylethyl (3S)-3-[(3-chloro-4-cyanophenyl)amino]-4-(methylamino)butanoate and the reaction was stirred at 65° C. LC-MS (ES) m/e 339.9 (M+H)+.

c) 2-chloro-4-{[(3S)-1-(1-ethylpropyl)-5-oxo-3-pyrrolidinyl]amino}benzonitrile

This compound was made using a procedure similar to Intermediate 1 (part j) except substituting methyl (3S)-3-[(3-chloro-4-cyanophenyl)amino]-4-[(1-ethylpropyl)amino]butanoate hydrochloride for methyl (3S)-3-[(3-chloro-4-cyanophenyl)amino]-4-(methylamino)butanoate, hydrochloride and the reaction was stirred for 24 h. LC-MS (ES) m/e 305.9 (M+H)+.

Intermediate 8

2-chloro-4-{[(3S)-5-oxo-1-propyl-3-pyrrolidinyl]amino}benzonitrile

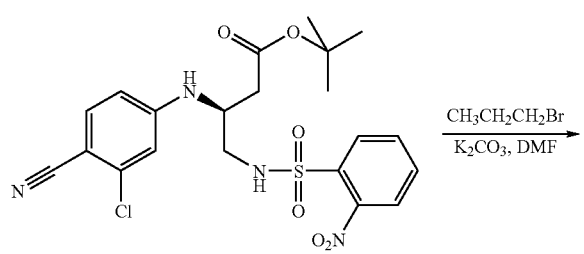

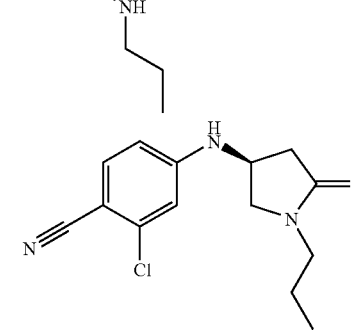

Intermediate 8 a) 1,1-Dimethylethyl (3S)-3-[(3-chloro-4-cyanophenyl)amino]-4-[[(2-nitrophenyl)sulfonyl](propyl)amino]butanoate This compound was made using a procedure similar to Intermediate 1 (part g) except substituting 1-bromobutane for MeI. LC-MS (ES) m/e 537.2 (M+H)+.

b) 1,1-Dimethylethyl (3S)-3-[(3-chloro-4-cyanophenyl)amino]-4-(propylamino)butanoate This compound was made using a procedure similar to Intermediate 1 (part h) except substituting 1,1-dimethylethyl (3S)-3-[(3-chloro-4-cyanophenyl)amino]-4-[[(2-nitrophenyl)sulfonyl](propyl)amino]butanoate for 1,1-dimethylethyl (3S)-3-[(3-chloro-4-cyanophenyl)amino]-4-{methyl[(2-nitrophenyl)sulfonyl]amino}butanoate. LC-MS (ES) m/e 352.6 (M+H)+.

c) Methyl (3S)-3-[(3-chloro-4-cyanophenyl)amino]-4-(propylamino)butanoate hydrochloride This compound was made using a procedure similar to Intermediate 1 (part i) except substituting 1,1-dimethylethyl (3S)-3-[(3-chloro-4-cyanophenyl)amino]-4-(propylamino) butanoate for 1,1-dimethylethyl (3S)-3-[(3-chloro-4-cyanophenyl)amino]-4-(methylamino)butanoate. LC-MS (ES) m/e 310.5 (M+H)+.

d) 2-Chloro-4-{[(3S)-5-oxo-1-propyl-3-pyrrolidinyl]amino}benzonitrile

This compound was made using a procedure similar to Intermediate 1 (part j) except substituting methyl (3S)-3-[(3-chloro-4-cyanophenyl)amino]-4-(propylamino)butanoate hydrochloride for methyl (3S)-3-[(3-chloro-4-cyanophenyl)amino]-4-(methylamino)butanoate, hydrochloride. LC-MS (ES) m/e 278.5 (M+H)+.

Intermediate 9

2-chloro-4-({(3S)-1-[2-(methyloxy)ethyl]-5-oxo-3-pyrrolidinyl}amino)benzonitrile

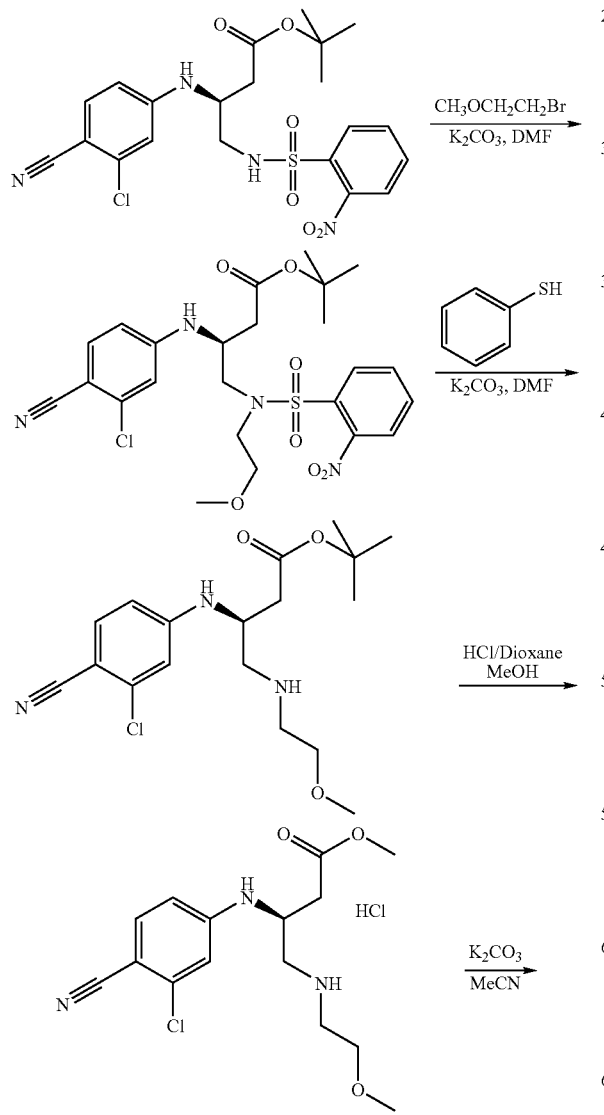

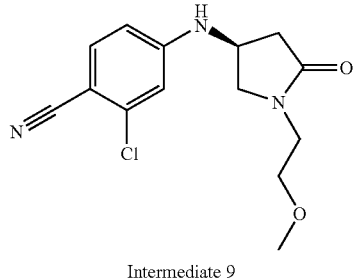

Intermediate 9 a) 1,1-Dimethylethyl (3S)-3-[(3-chloro-4-cyanophenyl)amino]-4-{[2-(methyloxy)ethyl][(2-nitrophenyl)sulfonyl]amino}butanoate This compound was made using a procedure similar to Intermediate 1 (part g) except substituting 2-bromoethyl methyl ether for MeI. LC-MS (ES) m/e 553.3 (M+H)+.

b) 1,1-Dimethylethyl (3S)-3-[(3-chloro-4-cyanophenyl)amino]-4-{[2-(methyloxy)ethyl]amino}butanoate This compound was made using a procedure similar to Intermediate 1 (part h) except substituting 1,1-dimethylethyl (3S)-3-[(3-chloro-4-cyanophenyl)amino]-4-{[2-(methyloxy)ethyl][(2-nitrophenyl)sulfonyl]amino}butanoate for 1,1-dimethylethyl (3S)-3-[(3-chloro-4-cyanophenyl)amino]-4-{methyl[(2-nitrophenyl)sulfonyl]amino}butanoate. LC-MS (ES) m/e 368.7 (M+H)+.

c) Methyl (3S)-3-[(3-chloro-4-cyanophenyl)amino]-4-{[2-(methyloxy)ethyl]amino}butanoate hydrochloride This compound was made using a procedure similar to Intermediate 1 (part i) except substituting 1,1-dimethylethyl (3S)-3-[(3-chloro-4-cyanophenyl)amino]-4-{[2-(methyloxy)ethyl]amino}butanoate for 1,1-dimethylethyl (3S)-3-[(3-chloro-4-cyanophenyl)amino]-4-(methylamino)butanoate. LC-MS (ES) m/e 326.6 (M+H)+.

d) 2-chloro-4-({(3S)-1-[2-(methyloxy)ethyl]-5-oxo-3-pyrrolidinyl}amino)benzonitrile This compound was made using a procedure similar to Intermediate 1 (part j) except substituting methyl (3S)-3-[(3-chloro-4-cyanophenyl)amino]-4-{[2-(methyloxy)ethyl]amino}butanoate hydrochloride for methyl (3S)-3-[(3-chloro-4-cyanophenyl)amino]-4-(methylamino)butanoate, hydrochloride. LC-MS (ES) m/e 294.5 (M+H)+.

Intermediate 10

2-chloro-4-{[(3S)-5-oxo-1-(2-propen-1-yl)-3-pyrrolidinyl]amino}benzonitrile

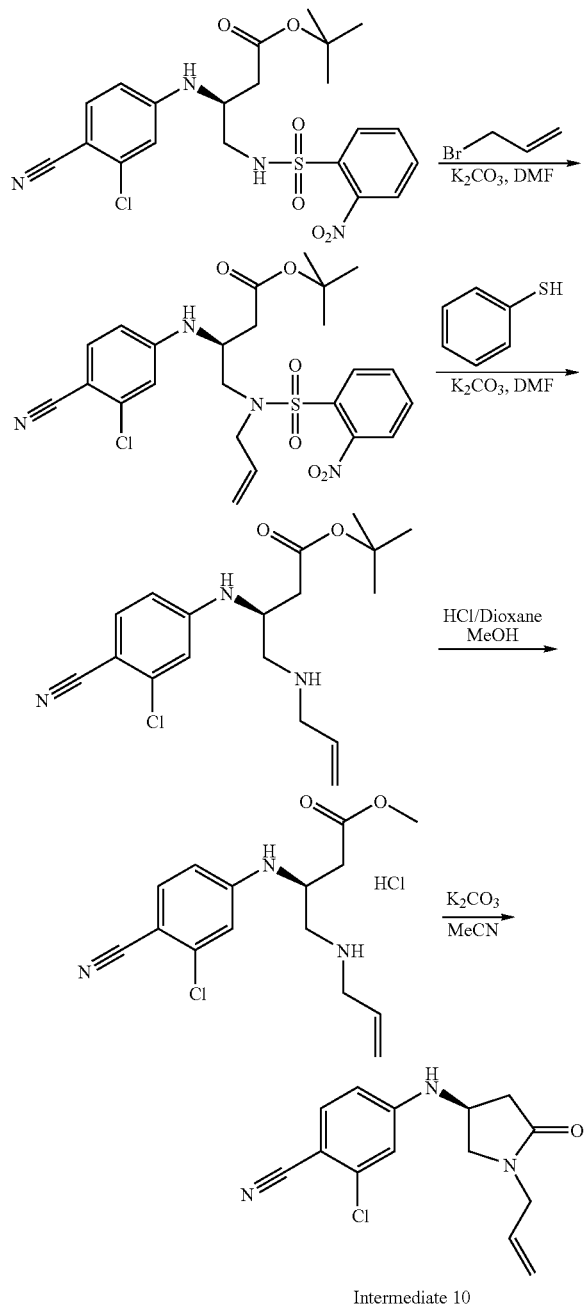

Intermediate 10 a) 1,1-Dimethylethyl (3S)-3-[(3-chloro-4-cyanophenyl)amino]-4-[[(2-nitrophenyl)sulfonyl](2-propen-1-yl)amino]butanoate This compound was made using a procedure similar to Intermediate 1 (part g) except substituting 3-bromo-1-propene for MeI. LC-MS (ES) m/e 535.8 (M+H)$^+$.

b) 1,1-Dimethylethyl (3S)-3-[(3-chloro-4-cyanophenyl)amino]-4-(2-propen-1-ylamino)butanoate This compound was made using a procedure similar to Intermediate 1 (part h) except substituting 1,1-dimethylethyl (3S)-3-[(3-chloro-4-cyanophenyl)amino]-4-[[(2-nitrophenyl)sulfonyl](2-propen-1-yl)amino]butanoate for 1,1-dimethylethyl (3S)-3-[(3-chloro-4-cyanophenyl)amino]-4-{methyl[(2-nitrophenyl)sulfonyl]amino}butanoate. LC-MS (ES) m/e 350.4 (M+H)$^+$.

c) Methyl (3S)-3-[(3-chloro-4-cyanophenyl)amino]-4-(2-propen-1-ylamino)butanoate hydrochloride This compound was made using a procedure similar to Intermediate 1 (part i) except substituting 1,1-Dimethylethyl (3S)-3-[(3-chloro-4-cyanophenyl)amino]-4-(2-propen-1-ylamino)butanoate for 1,1-dimethylethyl (3S)-3-[(3-chloro-4-cyanophenyl)amino]-4-(methylamino)butanoate. LC-MS (ES) m/e 308.5 (M+H)$^+$.

d) 2-Chloro-4-{[(3S)-5-oxo-1-(2-propen-1-yl)-3-pyrrolidinyl]amino}benzonitrile This compound was made using a procedure similar to Intermediate 1 (part j) except substituting methyl (3S)-3-[(3-chloro-4-cyanophenyl)amino]-4-(2-propen-1-ylamino)butanoate hydrochloride for methyl (3S)-3-[(3-chloro-4-cyanophenyl)amino]-4-(methylamino)butanoate, hydrochloride. LC-MS (ES) m/e 276.5 (M+H)$^+$.

Alternative Procedure for Preparation of 1,1-dimethylethyl (3S)-3-[(3-chloro-4-cyanophenyl)amino]-4-hydroxybutanoate

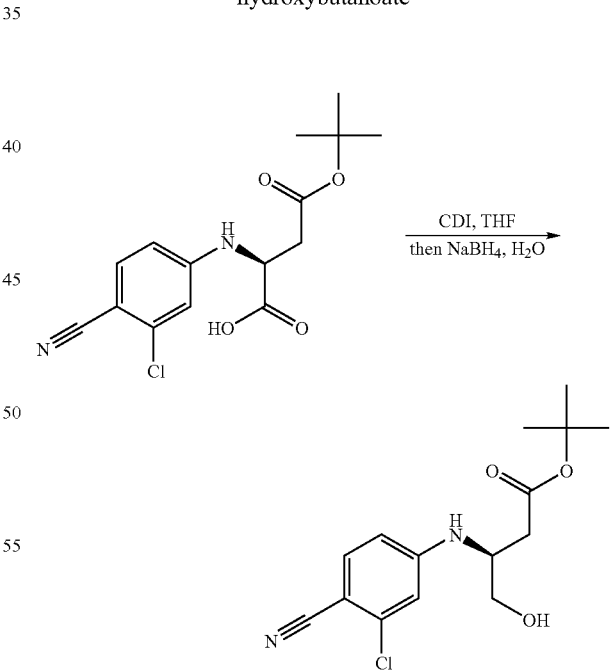

To a solution of (2S)-2-[(3-chloro-4-cyanophenyl)amino]-4-[(1,1-dimethylethyl)oxy]-4-oxobutanoic acid (115.0 g, 0.35 mol) in THF (300 mL) at −65° C. in a dry-ice/acetone bath was added portionwise carbonyl diimidazole (68.9 g, 0.43 mol) at such a rate as to maintain or decrease temperature. After the addition was complete, the reaction was stirred for an additional 1 h. This solution was transferred to a jacketed addition funnel containing dry ice in the jacket to maintain a solution temperature of −70° C., then added to a mixture of NaBH$_4$ (16.1 g, 0.43 mol), ice (600 mL), and THF (100 mL); the addition of the solution to the NaBH$_4$ mixture was carried out at such a rate that the temperature did not exceed 0° C. over the course of the addition. The resultant reaction mixture was stirred for an additional 1 h at 0° C. The reaction mixture was allowed to warm to ambient temperature, whereupon EtOAc (400 mL) and H$_2$O (400 mL) were added. The mixture was then acidified with 2 N HCl (approximately 800 mL) to pH 2.5. The organic layer was separated, and the aqueous phase was extracted twice with EtOAc (400 mL). The combined organics were washed with H$_2$O (400 mL), aqueous NaHCO$_3$ (400 mL), and brine (400 mL), dried over MgSO$_4$, then filtered, before the solvents were removed in vacuo. The resultant solid was dissolved in CH$_2$Cl$_2$ (200 mL), then hexane (400 mL) was added to the solution to precipitate the product. The resultant slurry was filtered, and the collected solids were placed under vacuum in an oven at ambient temperature to yield the desired product, 109.8 g (99.8%). LC-MS (ES) m/e 311.5 (M+H)$^+$.

EXAMPLE 1

2-Chloro-4-{[(2-chlorophenyl)methyl][(3S)-1-methyl-5-oxo-3-pyrrolidinyl]amino}benzonitrile

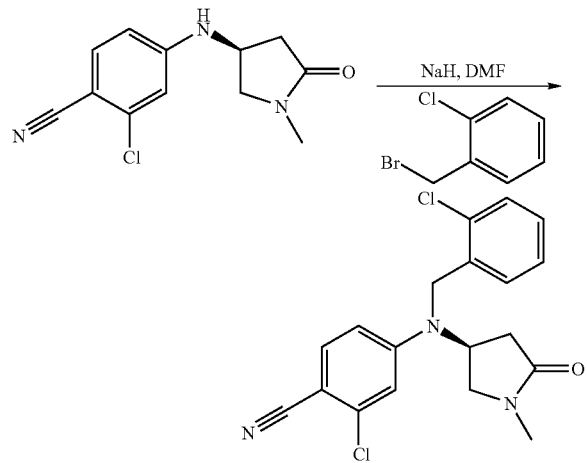

NaH (60% in mineral oil, 0.010 g, 0.26 mmol) was added to a solution of 2-chloro-4-{[(3S)-1-methyl-5-oxo-3-pyrrolidinyl]amino}benzonitrile (0.06 g, 0.24 mmol) in DMF (2 mL) at 0° C. under a N$_2$ atmosphere. After stirring for 10 min, 1-(bromomethyl)-2-chlorobenzene (0.054 g, 0.26 mmol) was added and the reaction mixture was stirred at 0° C. for 15 min. The reaction was quenched with H$_2$O and then partitioned between EtOAc and H$_2$O. The organic layer was dried over Na$_2$SO$_4$, filtered, and concentrated. The residue was purified via column chromatography with 5% EtOAc in hexane grading to 100% EtOAc in hexane to yield the titled compound (0.03 g, 37%) as a clear oil. $^1$H-NMR (CDCl$_3$) δ: 2.486 (1H, m), 2.797 (1H, m), 2.866 (3H, s), 3.383 (1H, m), 3.785 (1H, m), 4.563 (2H, m), 4.281 (1H, m), 6.519 (1H, dd, J=8.8 Hz, 2.8 Hz), 6.717 (1H, d, J=2.8 Hz), 6.757 (1H, dd, J=7.6 Hz, 1.2 Hz), 7.264 (2H, m), 7.420 (2H, m). LC-MS (ES) m/e 374.2 (M+H)$^+$.

EXAMPLE 2

2-Chloro-4-{[(3S)-1-methyl-5-oxo-3-pyrrolidinyl][(2-methylphenyl)methyl]amino}benzonitrile NaH (60% in mineral oil, 0.857 g, 21.4 mmol) was washed with pet ether (3×), suspended in DMF (50 mL), and cooled to 0° C. To this suspension was added a solution of 2-chloro-4-{[(3S)-1-methyl-5-oxo-3-pyrrolidinyl]amino}benzonitrile (5.08 g, 20.0 mmol) and DMF (25 mL) dropwise over 20 min. After stirring at 0° C. for 30 min, this solution was added dropwise to a pre-cooled (0° C.) solution of 1-(iodomethyl)-2-methylbenzene (7.0 g, 30.0 mmol) in DMF (75 mL) over 30 min. The reaction was stirred at 0° C. for an additional 20 min and then poured into a solution of aq. NH$_4$Cl (300 mL) and diethyl ether (300 mL). The layers were separated and the aqueous layer was extracted with Et$_2$O (2×300 mL). The organic extracts were washed with H$_2$O, aq. NaHSO$_3$, dried over Mg$_2$SO$_4$, filtered, and concentrated. The oil was triturated with isopropanol (1 mL) and diethyl ether (75 mL) and the solid filtered to give the titled compound (5.4 g., 76%) as a white solid. LC-MS (ES) m/e 354.5 (M+H)$^+$.

EXAMPLE 3

2-Chloro-4-{[(2-fluorophenyl)methyl][(3S)-1-(1-methylethyl)-5-oxo-3-pyrrolidinyl]amino}benzonitrile

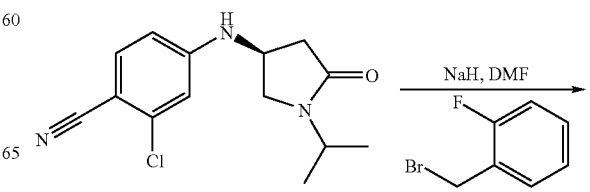

-continued

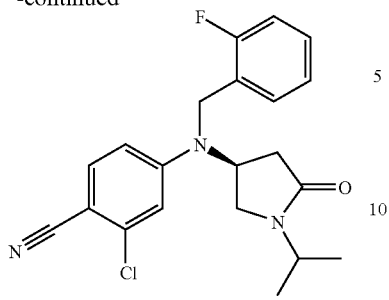

NaH (60% in mineral oil, 0.026 g, 0.65 mmol) was washed free of mineral oil and then suspended in DMF (3 mL) and cooled to −20° C. To this suspension was added a solution of 2-chloro-4-{[(3S)-1-(1-methylethyl)-5-oxo-3-pyrrolidinyl]amino}benzonitrile (0.120 g, 0.43 mmol). After stirring at −20° C. for 20 min, 1-(bromomethyl)-2-fluorobenzene (0.12 g, 0.65 mmol) in DMF (2 mL) was added and the reaction was stirred at −20° C. for 5 min and then at 0° C. for 5 min. The reaction was quenched with aqueous $NH_4Cl$, diluted with $H_2O$, and extracted with $Et_2O$ (2×). The organic extracts were washed with $H_2O$, dried over $Na_2SO_4$, filtered, and concentrated. The residue was purified via silica gel chromatography with 25% EtOAc in hexane grading to 100% EtOAc in hexane to afford the product (0.13 g, 79%) as a white solid. $^1$H-NMR ($CDCl_3$) δ: 1.137 (6H, dd, J=16.8 Hz, 6.8 Hz), 2.547 (1H, m), 2.842 (1H, m), 3.349 (1H, m), 3.749 (1H, m), 4.465 (1H, m), 4.588 (2H, m), 4.755 (1H, m), 6.566 (1H, d, J=8.8 Hz), 6.747 (1H, s), 7.031 (1H, m), 7.130 (2H, m), 7.325 (1H, m), 7.455 (1H, d, J=8.8 Hz). LC-MS (ES) m/e 386.4 $(M+H)^+$.

EXAMPLE 4

2-chloro-4-{[(3S)-1-(2-hydroxyethyl)-5-oxo-3-pyrrolidinyl][(2-methylphenyl)methyl]amino}benzonitrile

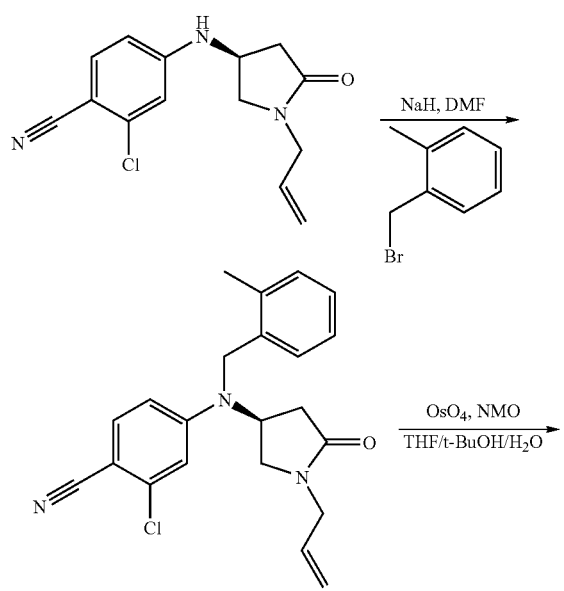

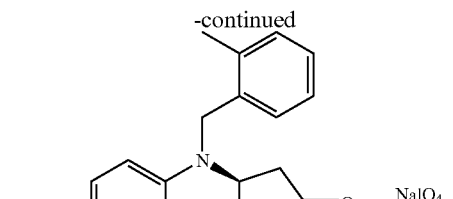

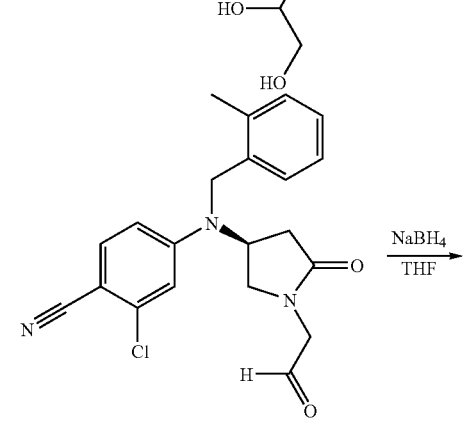

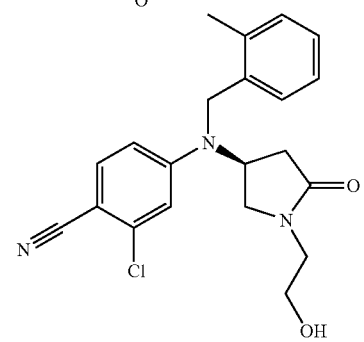

a) 2-Chloro-4-{[(2-methylphenyl)methyl][(3S)-5-oxo-1-(2-propen-1-yl)-3-pyrrolidinyl]amino}benzonitrile This compound was made using a procedure similar to example 2 except substituting 2-chloro-4-{[(3S)-5-oxo-1-(2-propen-1-yl)-3-pyrrolidinyl]amino}benzonitrile (Intermediate 10) for 2-chloro-4-{[(3S)-1-methyl-5-oxo-3-pyrrolidinyl]amino}benzonitrile. LC-MS (ES) m/e 380.6 $(M+H)^+$.

b) 2-Chloro-4-{[(3S)-1-(2,3-dihydroxypropyl)-5-oxo-3-pyrrolidinyl][(2-methylphenyl)methyl]amino}benzonitrile 2-Chloro-4-{[(2-methylphenyl)methyl][(3S)-5-oxo-1-(2-propen-1-yl)-3-pyrrolidinyl]amino}benzonitrile (30.0 mg, 0.08 mmol) and 4-methyl morpholine oxide (37.5 mg, 0.16 mmol) were dissolved in a mixture of THF/t-BuOH/$H_2O$ (0.5 mL/0.2 mL/0.1 mL). To this solution was added an osmium tetroxide/2-methyl-2-propanol solution (2.5 wt %, 81.3 mg, 0.008 mmol), and the mixture stirred at room temperature for 18 h. The reaction mixture was quenched with 5% $NaHSO_3$ (2 mL), and the organic layer was separated and concentrated to afford the desired product as a white solid (12.0 mg, 37% yield). LC-MS (ES) m/e 413.7 $(M+H)^+$.

c) 2-Chloro-4-{[(2-methylphenyl)methyl][(3S)-5-oxo-1-(2-oxoethyl)-3-pyrrolidinyl]amino}benzonitrile An aqueous solution of sodium periodate (0.25 M in H$_2$O, 12.8 mg, 0.06 mmol) was added to a solution of 2-chloro-4-{[(3S)-1-(2,3-dihydroxypropyl)-5-oxo-3-pyrrolidinyl][(2-methylphenyl)methyl]amino}benzonitrile (25.0 mg, 0.06 mmol) in THF. After stirring at room temperature for 30 min, the reaction mixture was extracted three times with ethyl acetate (5 mL). The organics were dried over anhydrous MgSO$_4$ and concentrated to give the titled compound as white foam. The crude material was immediately used in the next step.

d) 2-Chloro-4-{[(3S)-1-(2-hydroxyethyl)-5-oxo-3-pyrrolidinyl][(2-methylphenyl)methyl]amino}benzonitrile 2-Chloro-4-{[(2-methylphenyl)methyl][(3S)-5-oxo-1-(2-oxoethyl)-3-pyrrolidinyl]amino}benzonitrile from the previous step was dissolved in THF, and NaBH$_4$ (1.2 eq) was added. After stirring at room temperature for 2 h, the reaction mixture was quenched with H$_2$O and extracted three times with ethyl acetate (5 mL). The organics were dried over anhydrous MgSO$_4$ and concentrated to give the titled compound as white solid (3.5 g, 33% for two steps). LC-MS (ES) m/e 384.6 (M+H)$^+$.

EXAMPLE 5

2-chloro-4-{[(3S)-1-(3-hydroxypropyl)-5-oxo-3-pyrrolidinyl][(2-methylphenyl)methyl]amino}benzonitrile

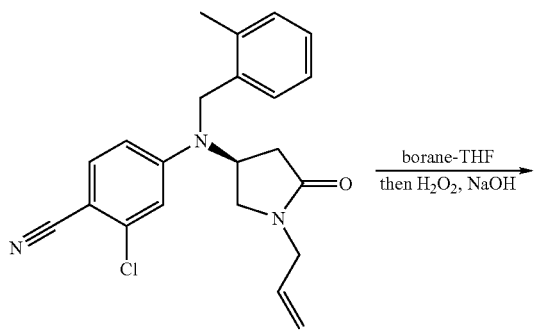

borane-THF
then H$_2$O$_2$, NaOH

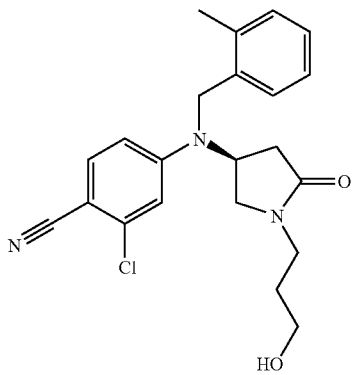

Borane-THF (1.0 M, 0.25 mL, 0.25 mmol) was added to a solution of 2-chloro-4-{[(2-methylphenyl)methyl][(3S)-5-oxo-1-(2-propen-1-yl)-3-pyrrolidinyl]amino}benzonitrile (20.0 mg, 0.05 mmol), and the reaction mixture stirred at room temperature overnight. Upon complete consumption of the starting material; the reaction mixture was diluted with THF (5 mL), and H$_2$O (1.0 mL, 2.6 mmol) was added dropwise at 0° C. The mixture then warmed to room temperature over 30 min. Hydrogen peroxide (30 wt % in H$_2$O, 36.2 mg, 0.32 mmol) and 2 N NaOH (0.06 mL, 0.12 mmol) were added at 0° C., and the resulting mixture stirred at 25° C. for 1 h and at 60° C. for 2 h. The reaction mixture was cooled and extracted twice with EtOAc. The combined organic extracts were dried over Na$_2$SO$_4$ and concentrated to give a crude mixture of the desired terminal alcohol and secondary alcohol racemate. The title compound (3.0 mg, 14% yield) was isolated as a white solid by HPLC purification: 30×100 Xterra Prep, eluting with water (solvent A) and acetonitrile (solvent B), no TFA; 40 to 100% (solvent B) over 17 min at a flow rate of 30 mL/min. LC-MS (ES) m/e 398.7 (M+H)$^+$.

The following table illustrates compounds that were prepared in accordance with procedures as indicated. (Int=intermediate used; proced=example number that was generally followed, using the appropriate electrophile.)

| Ex # | Int | Proced. | Structure | m/z | Name |
|---|---|---|---|---|---|
| 6 | 1 | 1 | 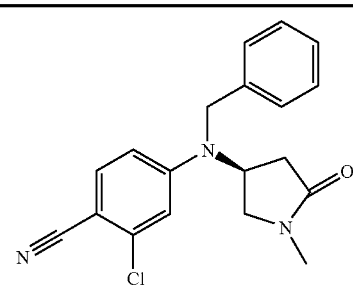 | 340.2 | 2-chloro-4-[[(3S)-1-methyl-5-oxo-3-pyrrolidinyl](phenylmethyl)amino]benzonitrile |

-continued

| Ex # | Int | Proced. | Structure | m/z | Name |
|---|---|---|---|---|---|
| 7 | 1 | 1 | 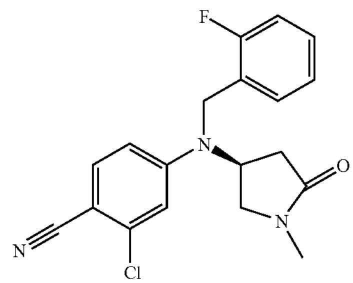 | 358.2 | 2-chloro-4-{[(2-fluorophenyl)methyl][(3S)-1-methyl-5-oxo-3-pyrrolidinyl]amino}benzonitrile |
| 8 | 1 | 1 | 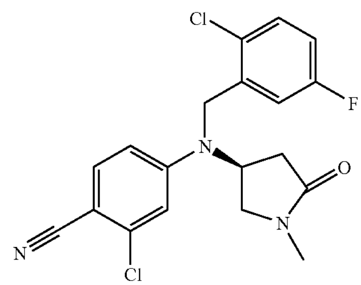 | 392.4 | 2-chloro-4-{[(2-chloro-5-fluorophenyl)methyl][(3S)-1-methyl-5-oxo-3-pyrrolidinyl]amino}benzonitrile |
| 9 | 1 | 1 | 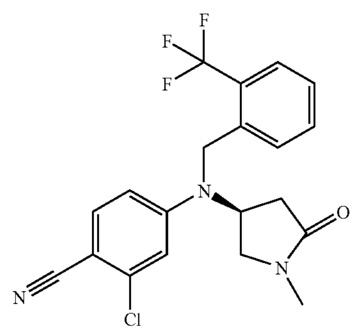 | 408.6 | 2-chloro-4-([(3S)-1-methyl-5-oxo-3-pyrrolidinyl]{[2-(trifluoromethyl)phenyl]methyl}amino)benzonitrile |
| 10 | 1 | 1 | 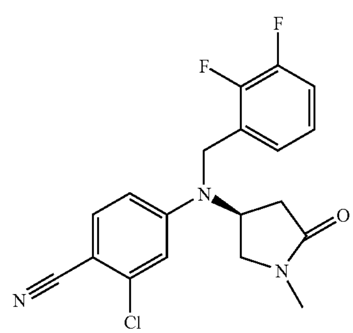 | 376.6 | 2-chloro-4-{[(2,3-difluorophenyl)methyl][(3S)-1-methyl-5-oxo-3-pyrrolidinyl]amino}benzonitrile |
| 11 | 1 | 1 | 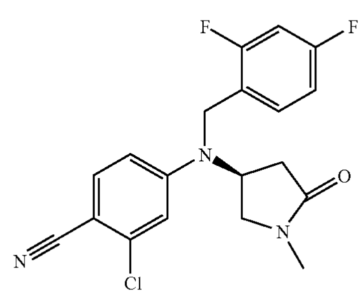 | 376.6 | 2-chloro-4-{[(2,4-difluorophenyl)methyl][(3S)-1-methyl-5-oxo-3-pyrrolidinyl]amino}benzonitrile |

| Ex # | Int | Proced. | Structure | m/z | Name |
|---|---|---|---|---|---|
| 12 | 1 | 2 | 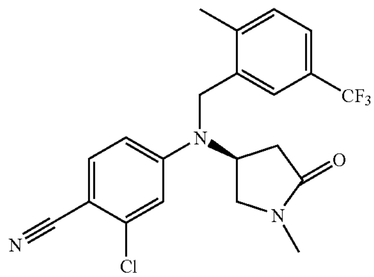 | 422.6 | 2-chloro-4-([[(3S)-1-methyl-5-oxo-3-pyrrolidinyl]{[2-methyl-5-(trifluoromethyl)phenyl]methyl}amino)benzonitrile |
| 13 | 1 | 2 | 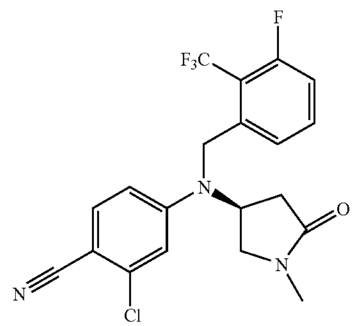 | 426.6 | 2-chloro-4-{{[3-fluoro-2-(trifluoromethyl)phenyl]methyl}[(3S)-1-methyl-5-oxo-3-pyrrolidinyl]amino}benzonitrile |
| 14 | 1 | 2 | 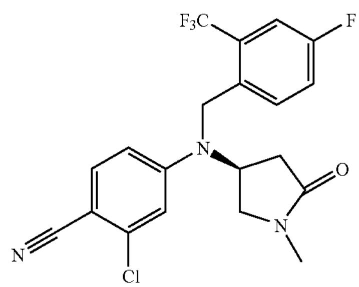 | 426.6 | 2-chloro-4-{{[4-fluoro-2-(trifluoromethyl)phenyl]methyl}[(3S)-1-methyl-5-oxo-3-pyrrolidinyl]amino}benzonitrile |
| 15 | 1 | 2 | 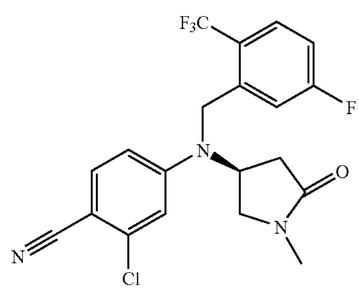 | 426.6 | 22-chloro-4-{{[5-fluoro-2-(trifluoromethyl)phenyl]methyl}[(3S)-1-methyl-5-oxo-3-pyrrolidinyl]amino}benzonitrile |
| 16 | 1 | 2 | 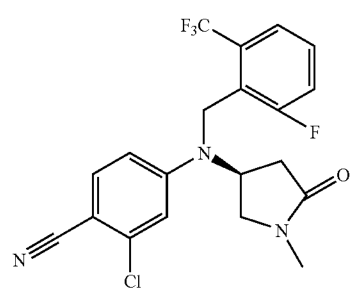 | 426.6 | 2-chloro-4-{{[2-fluoro-6-(trifluoromethyl)phenyl]methyl}[(3S)-1-methyl-5-oxo-3-pyrrolidinyl]amino }benzonitrile |

-continued

| Ex # | Int | Proced. | Structure | m/z | Name |
|---|---|---|---|---|---|
| 17 | 1 | 2 | 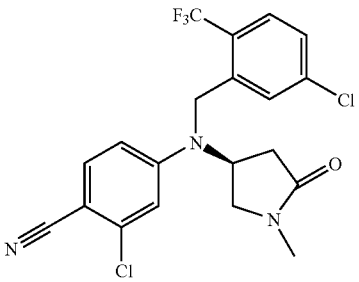 | 443.0 | 2-chloro-4-{{[5-chloro-2-(trifluoromethyl)phenyl]methyl}[(3S)-1-methyl-5-oxo-3-pyrrolidinyl]amino}benzonitrile |
| 18 | 1 | 2 | 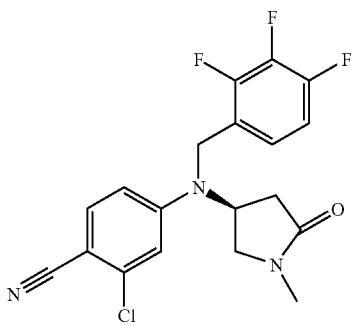 | 394.6 | 2-chloro-4-{[(3S)-1-methyl-5-oxo-3-pyrrolidinyl][(2,3,4-trifluorophenyl)methyl]amino}benzonitrile |
| 19 | 1 | 2 | 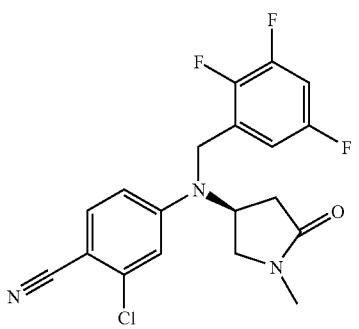 | 394.6 | 2-chloro-4-{[(3S)-1-methyl-5-oxo-3-pyrrolidinyl][(2,3,5-trifluorophenyl)methyl]amino}benzonitrile |
| 20 | 1 | 2 | 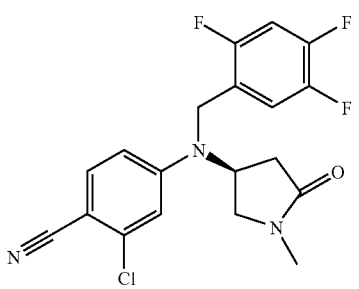 | 394.6 | 2-chloro-4-{[(3S)-1-methyl-5-oxo-3-pyrrolidinyl][(2,4,5-trifluorophenyl)methyl]amino}benzonitrile |
| 21 | 1 | 2 | 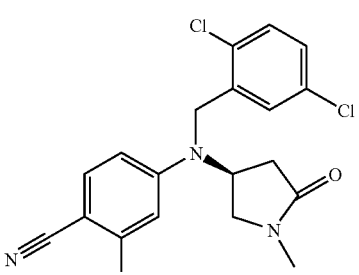 | 409.5 | 2-chloro-4-{[(2,5-dichlorophenyl)methyl][(3S)-1-methyl-5-oxo-3-pyrrolidinyl]amino}benzonitrile |

| Ex # | Int | Proced. | Structure | m/z | Name |
|---|---|---|---|---|---|
| 22 | 1 | 2 | 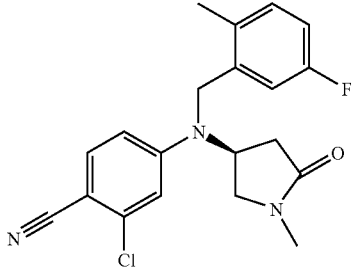 | 372.6 | 2-chloro-4-{[(5-fluoro-2-methylphenyl)methyl][(3S)-1-methyl-5-oxo-3-pyrrolidinyl]amino}benzonitrile |
| 23 | 1 | 2 | 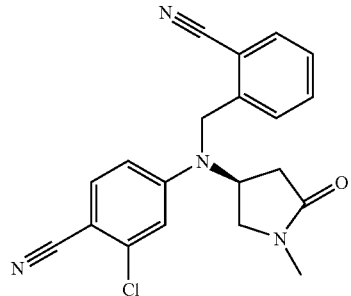 | 365.6 | 2-chloro-4-{[(2-cyanophenyl)methyl][(3S)-1-methyl-5-oxo-3-pyrrolidinyl]amino}benzonitrile |
| 24 | 1 | 2 | 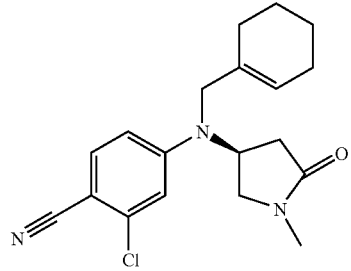 | 344.3 | 2-chloro-4-{(1-cyclohexen-1-ylmethyl)[(3S)-1-methyl-5-oxo-3-pyrrolidinyl]amino}benzonitrile |
| 25 | 3 | 1 | 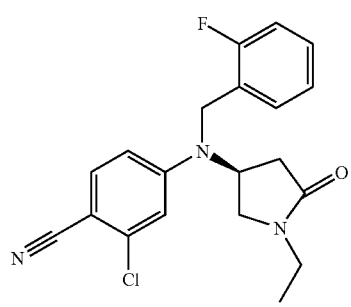 | 372.4 | 2-chloro-4-{[(3S)-1-ethyl-5-oxo-3-pyrrolidinyl][(2-fluorophenyl)methyl]amino}benzonitrile |
| 26 | 3 | 2 | 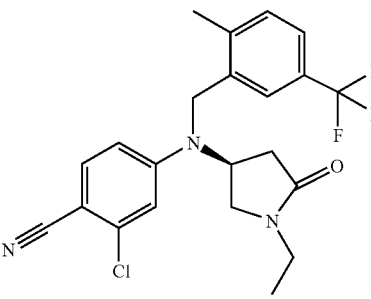 | 436.5 | 2-chloro-4-([(3S)-1-ethyl-5-oxo-3-pyrrolidinyl]{[2-methyl-5-(trifluoromethyl)phenyl]methyl}amino)benzonitrile |

| Ex # | Int | Proced. | Structure | m/z | Name |
|---|---|---|---|---|---|
| 27 | 3 | 2 | 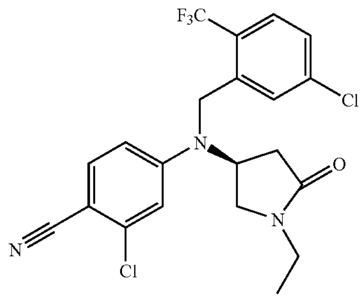 | 456.2 | 2-chloro-4-{{[5-chloro-2-(trifluoromethyl)phenyl]methyl}[(3S)-1-ethyl-5-oxo-3-pyrrolidinyl]amino}benzonitrile |
| 28 | 3 | 2 | 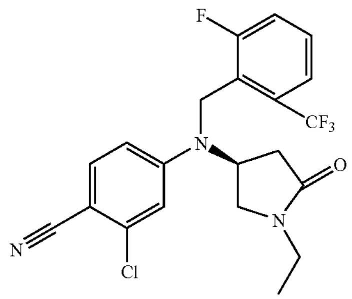 | 440.4 | 2-chloro-4-([(3S)-1-ethyl-5-oxo-3-pyrrolidinyl]{[2-fluoro-6-(trifluoromethyl)phenyl]methyl}amino)benzonitrile |
| 29 | 3 | 2 | 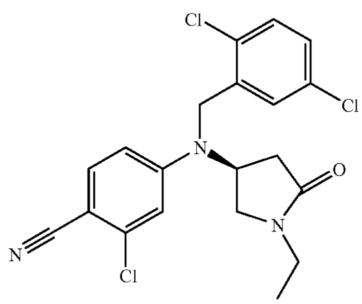 | 422.2 | 2-chloro-4-{[(2,5-dichlorophenyl)methyl][(3S)-1-ethyl-5-oxo-3-pyrrolidinyl]amino}benzonitrile |
| 30 | 3 | 2 | 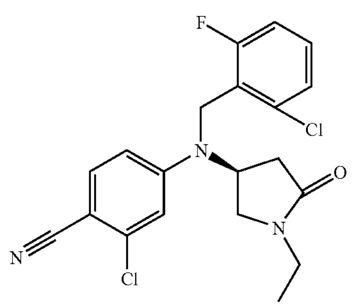 | 405.8 | 2-chloro-4-{[(2-chloro-6-fluorophenyl)methyl][(3S)-1-ethyl-5-oxo-3-pyrrolidinyl]amino}benzonitrile |
| 31 | 3 | 2 | 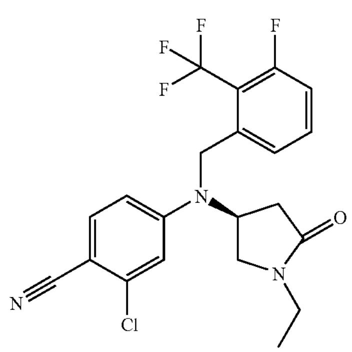 | 440.4 | 2-chloro-4-([(3S)-1-ethyl-5-oxo-3-pyrrolidinyl]{[3-fluoro-2-(trifluoromethyl)phenyl]methyl}amino)benzonitrile |

-continued

| Ex # | Int | Proced. | Structure | m/z | Name |
|---|---|---|---|---|---|
| 32 | 3 | 2 | 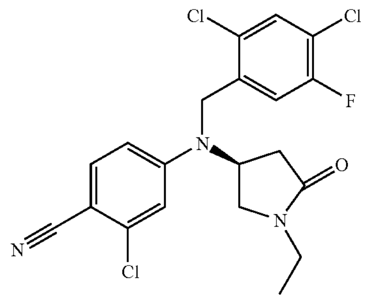 | 439.7 | 2-chloro-4-{[(2,4-dichloro-5-fluorophenyl)methyl][(3S)-1-ethyl-5-oxo-3-pyrrolidinyl]amino}benzonitrile |
| 33 | 3 | 2 | 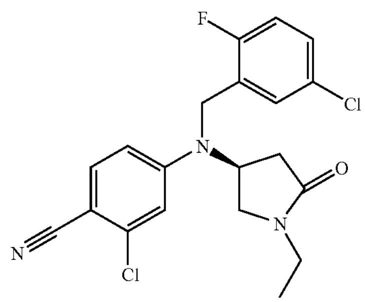 | 406.0 | 2-chloro-4-{[(5-chloro-2-fluorophenyl)methyl][(3S)-1-ethyl-5-oxo-3-pyrrolidinyl]amino}benzonitrile |
| 34 | 3 | 2 | 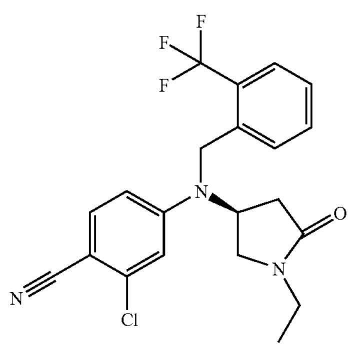 | 422.3 | 2-chloro-4-([(3S)-1-ethyl-5-oxo-3-pyrrolidinyl]{[2-(trifluoromethyl)phenyl]methyl}amino)benzonitrile |
| 35 | 3 | 2 | 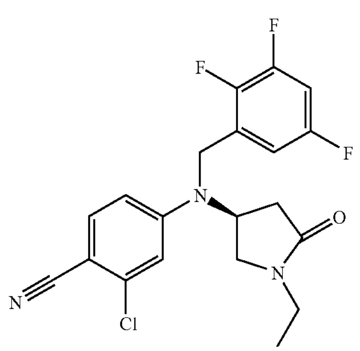 | 407.8 | 2-chloro-4-{[(3S)-1-ethyl-5-oxo-3-pyrrolidinyl][(2,3,5-trifluorophenyl)methyl]amino}benzonitrile |

| Ex # | Int | Proced. | Structure | m/z | Name |
|---|---|---|---|---|---|
| 36 | 3 | 2 | 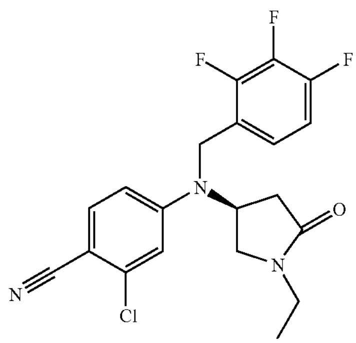 | 406.1 | 2-chloro-4-{[(3S)-1-ethyl-5-oxo-3-pyrrolidinyl][(2,3,4-trifluorophenyl)methyl]amino}benzonitrile |
| 37 | 3 | 2 | 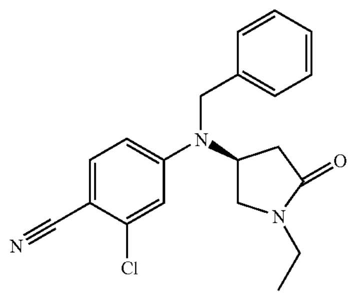 | 353.7 | 2-chloro-4-[[(3S)-1-ethyl-5-oxo-3-pyrrolidinyl](phenylmethyl)amino]benzonitrile |
| 38 | 3 | 2 | 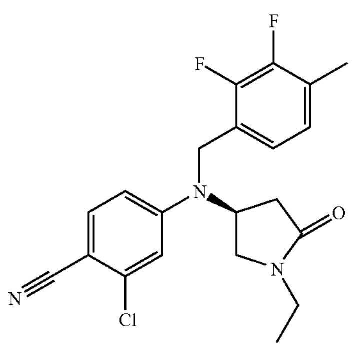 | 403.7 | 2-chloro-4-{[(2,3-difluoro-4-methylphenyl)methyl][(3S)-1-ethyl-5-oxo-3-pyrrolidinyl]amino}benzonitrile |
| 39 | 3 | 2 | 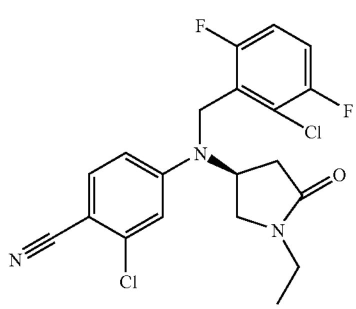 | 425.8 | 2-chloro-4-{[(2-chloro-3,6-difluorophenyl)methyl][(3S)-1-ethyl-5-oxo-3-pyrrolidinyl]amino}benzonitrile |
| 40 | 3 | 1 | 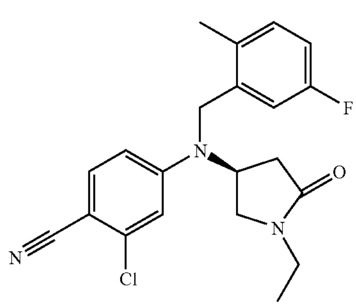 | 385.8 | 2-chloro-4-{[(3S)-1-ethyl-5-oxo-3-pyrrolidinyl][(5-fluoro-2-methylphenyl)methyl]amino}benzonitrile |

| Ex # | Int | Proced. | Structure | m/z | Name |
|---|---|---|---|---|---|
| 41 | 3 | 1 | 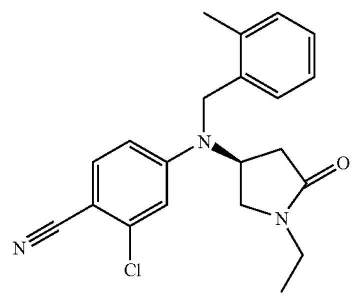 | 368.4 | 2-chloro-4-{[(3S)-1-ethyl-5-oxo-3-pyrrolidinyl][(2-methylphenyl)methyl]amino}benzonitrile |
| 42 | 3 | 1 | 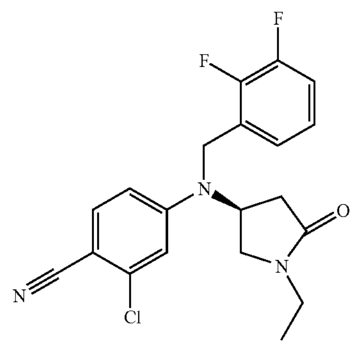 | 390.4 | 2-chloro-4-{[(2,3-difluorophenyl)methyl][(3S)-1-ethyl-5-oxo-3-pyrrolidinyl]amino}benzonitrile |
| 43 | 3 | 1 | 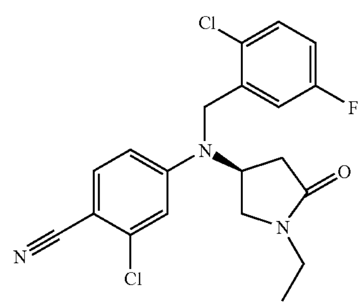 | 406.6 | 2-chloro-4-{[(2-chloro-5-fluorophenyl)methyl][(3S)-1-ethyl-5-oxo-3-pyrrolidinyl]amino}benzonitrile |
| 44 | 3 | 1 | 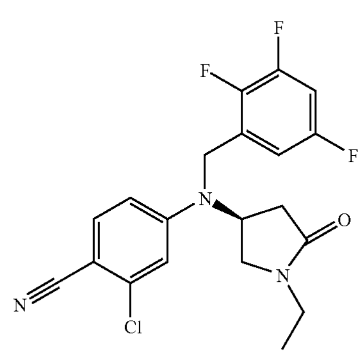 | 408.5 | 2-chloro-4-{[(3S)-1-ethyl-5-oxo-3-pyrrolidinyl][(2,3,5-trifluorophenyl)methyl]amino}benzonitrile |

| Ex # | Int | Proced. | Structure | m/z | Name |
|---|---|---|---|---|---|
| 45 | 3 | 1 | 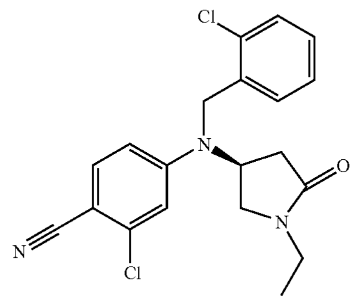 | 388.5 | 2-chloro-4-{[(2-chlorophenyl)methyl][(3S)-1-ethyl-5-oxo-3-pyrrolidinyl]amino}benzonitrile |
| 46 | 3 | 1 | 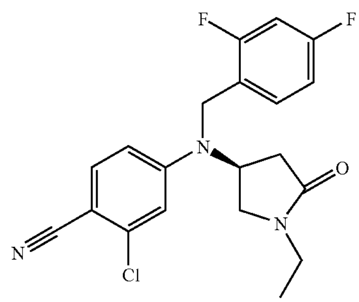 | 390.3 | 2-chloro-4-{[(2,4-difluorophenyl)methyl][(3S)-1-ethyl-5-oxo-3-pyrrolidinyl]amino}benzonitrile |
| 47 | 3 | 1 | 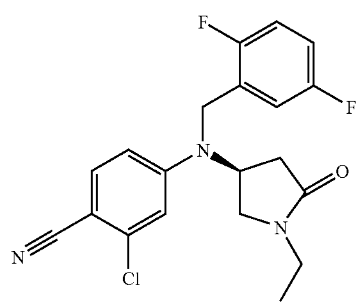 | 390.4 | 2-chloro-4-{[(2,5-difluorophenyl)methyl][(3S)-1-ethyl-5-oxo-3-pyrrolidinyl]amino}benzonitrile |
| 48 | 3 | 1 | 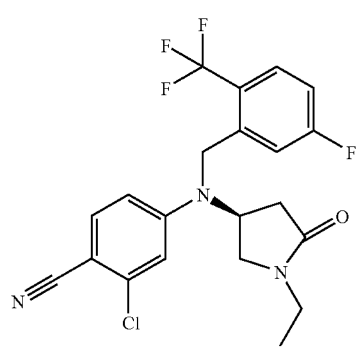 | 440.4 | 2-chloro-4-([(3S)-1-ethyl-5-oxo-3-pyrrolidinyl]{[5-fluoro-2-(trifluoromethyl)phenyl]methyl}amino)benzonitrile |

-continued

| Ex # | Int | Proced. | Structure | m/z | Name |
|---|---|---|---|---|---|
| 49 | 3 | 1 | 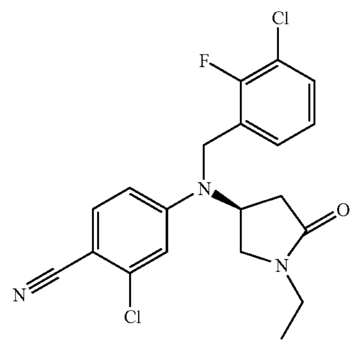 | 406.6 | 2-chloro-4-{[(3-chloro-2-fluorophenyl)methyl][(3S)-1-ethyl-5-oxo-3-pyrrolidinyl]amino}benzonitrile |
| 50 | 2 | 3 | 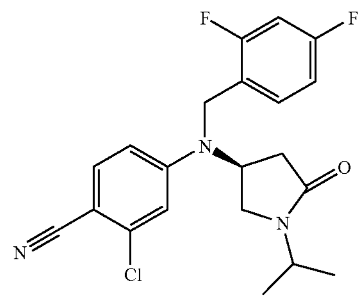 | 404.4 | 2-chloro-4-{[(2,4-difluorophenyl)methyl][(3S)-1-(1-methylethyl)-5-oxo-3-pyrrolidinyl]amino}benzonitrile |
| 51 | 2 | 3 | 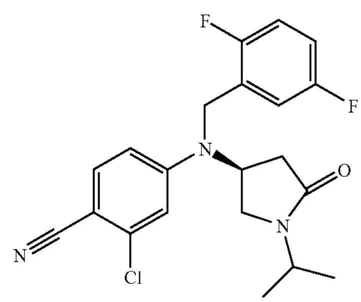 | 404.4 | 2-chloro-4-{[(2,5-difluorophenyl)methyl][(3S)-1-(1-methylethyl)-5-oxo-3-pyrrolidinyl]amino}benzonitrile |
| 52 | 2 | 3 | 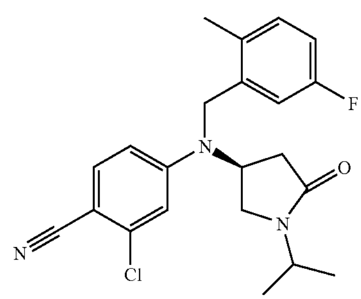 | 400.4 | 2-chloro-4-{[(5-fluoro-2-methylphenyl)methyl][(3S)-1-(1-methylethyl)-5-oxo-3-pyrrolidinyl]amino}benzonitrile |
| 53 | 2 | 3 | 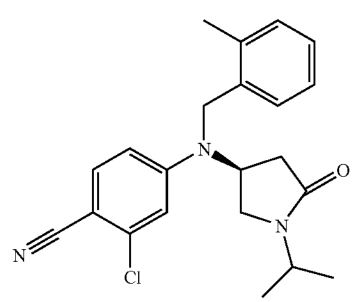 | 382.5 | 2-chloro-4-{[(3S)-1-(1-methylethyl)-5-oxo-3-pyrrolidinyl][(2-methylphenyl)methyl]amino}benzonitrile |

-continued

| Ex # | Int | Proced. | Structure | m/z | Name |
|---|---|---|---|---|---|
| 54 | 2 | 3 | 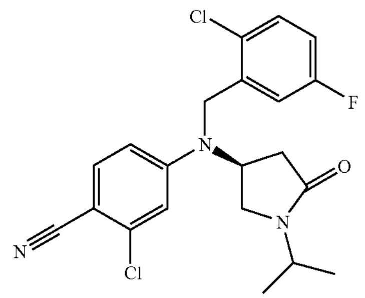 | 420.4 | 2-chloro-4-{[(2-chloro-5-fluorophenyl)methyl][(3S)-1-(1-methylethyl)-5-oxo-3-pyrrolidinyl]amino}benzonitrile |
| 55 | 2 | 3 | 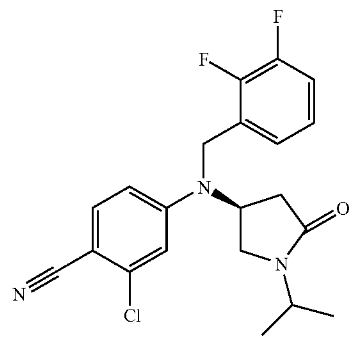 | 404.4 | 2-chloro-4-{[(2,3-difluorophenyl)methyl][(3S)-1-(1-methylethyl)-5-oxo-3-pyrrolidinyl]amino}benzonitrile |
| 56 | 2 | 3 | 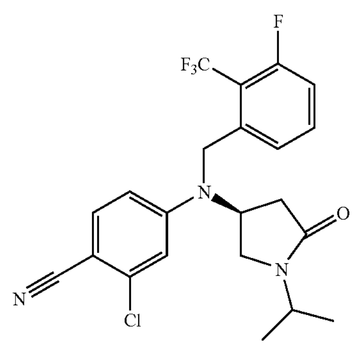 | 454.2 | 2-chloro-4-{{[3-fluoro-2-(trifluoromethyl)phenyl]methyl}[(3S)-1-(1-methylethyl)-5-oxo-3-pyrrolidinyl]amino}benzonitrile |
| 57 | 2 | 3 | 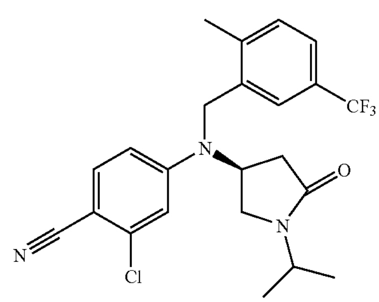 | 450.2 | 2-chloro-4-([(3S)-1-(1-methylethyl)-5-oxo-3-pyrrolidinyl]{[2-methyl-5-(trifluoromethyl)phenyl]methyl}amino)benzonitrile |
| 58 | 2 | 3 | 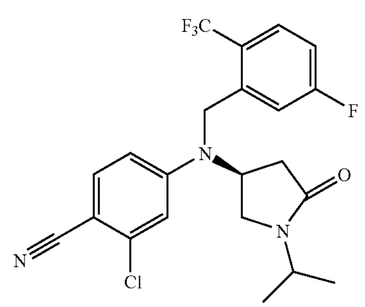 | 454.2 | 2-chloro-4-{{[5-fluoro-2-(trifluoromethyl)phenyl]methyl}[(3S)-1-(1-methylethyl)-5-oxo-3-pyrrolidinyl]amino}benzonitrile |

-continued

| Ex # | Int | Proced. | Structure | m/z | Name |
|---|---|---|---|---|---|
| 59 | 2 | 3 | 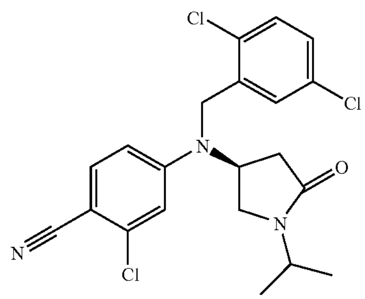 | 436.3 | 2-chloro-4-{[(2,5-dichlorophenyl)methyl][(3S)-1-(1-methylethyl)-5-oxo-3-pyrrolidinyl]amino}benzonitrile |
| 60 | 2 | 3 | 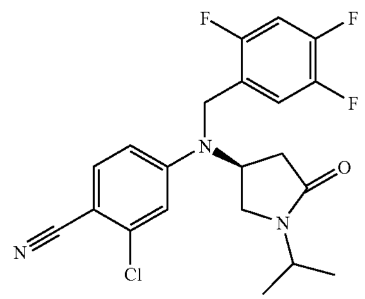 | 422.2 | 2-chloro-4-{[(3S)-1-(1-methylethyl)-5-oxo-3-pyrrolidinyl][(2,4,5-trifluorophenyl)methyl]amino}benzonitrile |
| 61 | 2 | 3 | 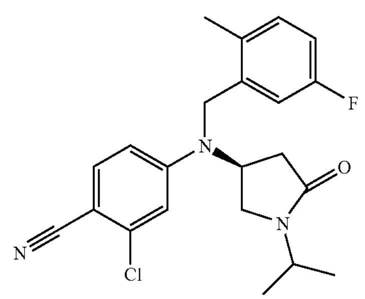 | 400.2 | 2-chloro-4-{[(5-fluoro-2-methylphenyl)methyl][(3S)-1-(1-methylethyl)-5-oxo-3-pyrrolidinyl]amino}benzonitrile |
| 62 | 2 | 3 | 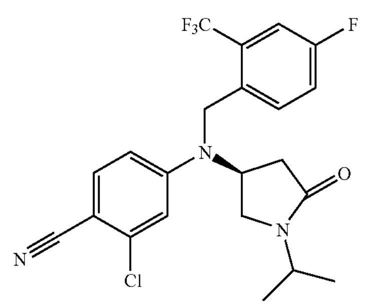 | 454.1 | 2-chloro-4-{{[4-fluoro-2-(trifluoromethyl)phenyl]methyl}[(3S)-1-(1-methylethyl)-5-oxo-3-pyrrolidinyl]amino}benzonitrile |
| 63 | 2 | 3 | 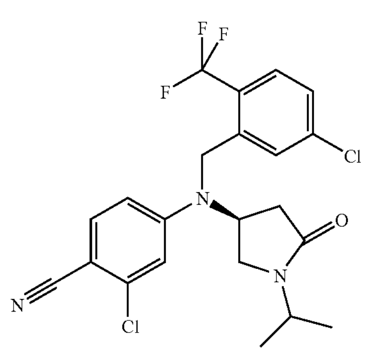 | 472.4 | 2-chloro-4-{{[5-chloro-2-(trifluoromethyl)phenyl]methyl}[(3S)-1-(1-methylethyl)-5-oxo-3-pyrrolidinyl]amino}benzonitrile |

| Ex # | Int | Proced. | Structure | m/z | Name |
|---|---|---|---|---|---|
| 64 | 2 | 3 | 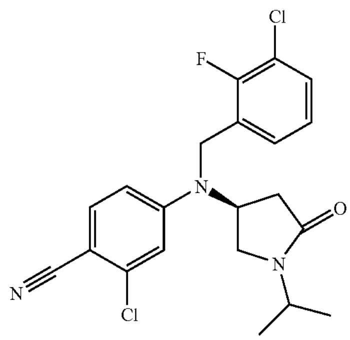 | 420.3 | 2-chloro-4-{[(3-chloro-2-fluorophenyl)methyl][(3S)-1-(1-methylethyl)-5-oxo-3-pyrrolidinyl]amino}benzonitrile |
| 65 | 2 | 2 | 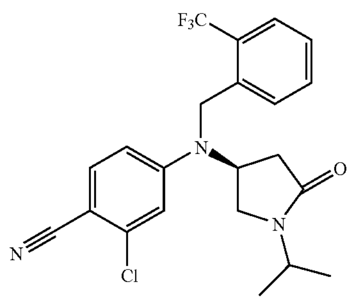 | 436 | 2-chloro-4-([[(3S)-1-(1-methylethyl)-5-oxo-3-pyrrolidinyl]{[2-(trifluoromethyl)phenyl]methyl}amino)benzonitrile |
| 66 | 2 | 2 | 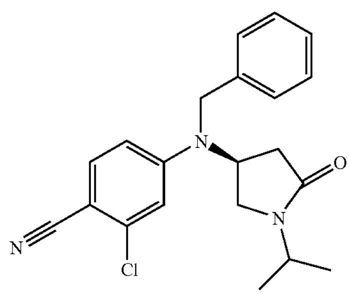 | 368 | 2-chloro-4-[[(3S)-1-(1-methylethyl)-5-oxo-3-pyrrolidinyl](phenylmethyl)amino]benzonitrile |
| 67 | 2 | 2 | 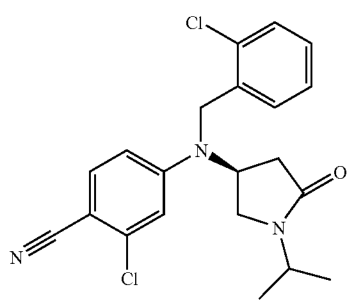 | 402 | 2-chloro-4-{[(2-chlorophenyl)methyl][(3S)-1-(1-methylethyl)-5-oxo-3-pyrrolidinyl]amino}benzonitrile |
| 68 | 4 | 3 | 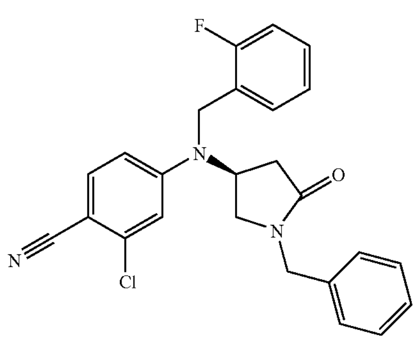 | 434.5 | 2-chloro-4-{[(2-fluorophenyl)methyl][(3S)-5-oxo-1-(phenylmethyl)-3-pyrrolidinyl]amino}benzonitrile |

-continued

| Ex # | Int | Proced. | Structure | m/z | Name |
|---|---|---|---|---|---|
| 69 | 5 | 3 | 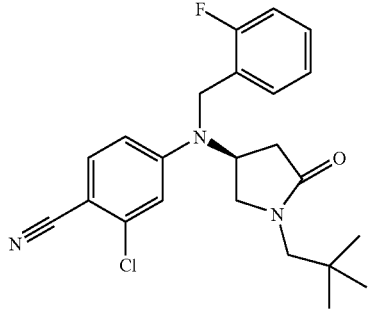 | 414 | 2-chloro-4-{[(3S)-1-(2,2-dimethylpropyl)-5-oxo-3-pyrrolidinyl][(2-fluorophenyl)methyl]amino}benzonitrile |
| 70 | 6 | 2 | 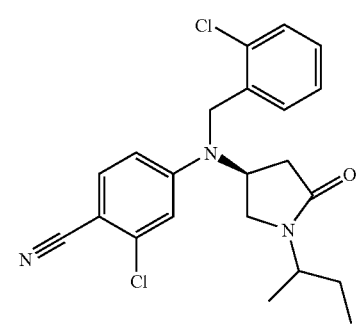 | 416.4 | 2-chloro-4-{[(2-chlorophenyl)methyl][(3S)-1-(1-methylpropyl)-5-oxo-3-pyrrolidinyl]amino}benzonitrile |
| 71 | 6 | 2 | 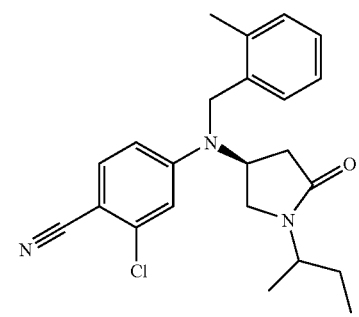 | 396.4 | 2-chloro-4-{[(2-methylphenyl)methyl][(3S)-1-(1-methylpropyl)-5-oxo-3-pyrrolidinyl]amino}benzonitrile |
| 72 | 6 | 2 | 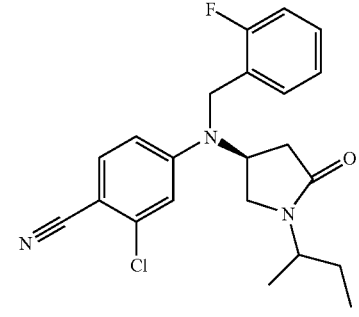 | 400.4 | 2-chloro-4-{[(2-fluorophenyl)methyl][(3S)-1-(1-methylpropyl)-5-oxo-3-pyrrolidinyl]amino}benzonitrile |

| Ex # | Int | Proced. | Structure | m/z | Name |
|---|---|---|---|---|---|
| 73 | 6 | 2 | 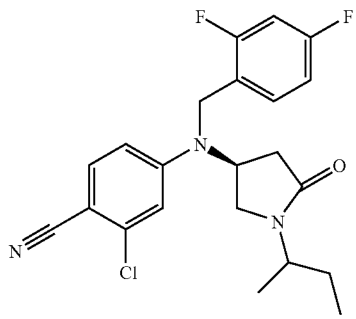 | 418.5 | 2-chloro-4-{[(2,4-difluorophenyl)methyl][(3S)-1-(1-methylpropyl)-5-oxo-3-pyrrolidinyl]amino}benzonitrile |
| 74 | 6 | 2 | 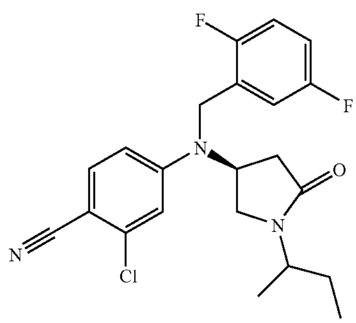 | 418.5 | 2-chloro-4-{[(2,5-difluorophenyl)methyl][(3S)-1-(1-methylpropyl)-5-oxo-3-pyrrolidinyl]amino}benzonitrile |
| 75 | 6 | 2 | 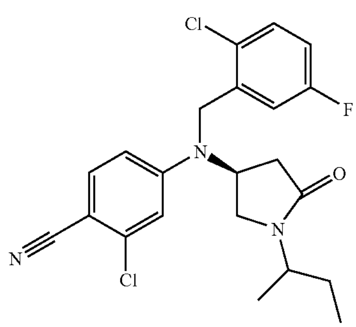 | 434.6 | 2-chloro-4-{[(2-chloro-5-fluorophenyl)methyl][(3S)-1-(1-methylpropyl)-5-oxo-3-pyrrolidinyl]amino}benzonitrile |
| 76 | 6 | 2 | 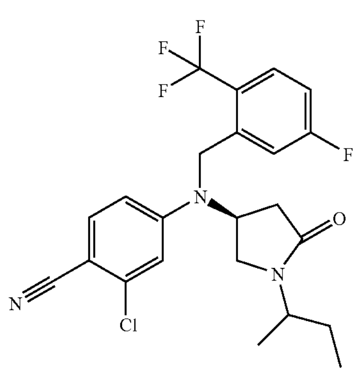 | 468.4 | 2-chloro-4-{{[5-fluoro-2-(trifluoromethyl)phenyl]methyl}[(3S)-1-(1-methylpropyl)-5-oxo-3-pyrrolidinyl]amino}benzonitrile |

| Ex # | Int | Proced. | Structure | m/z | Name |
| --- | --- | --- | --- | --- | --- |
| 77 | 6 | 2 | 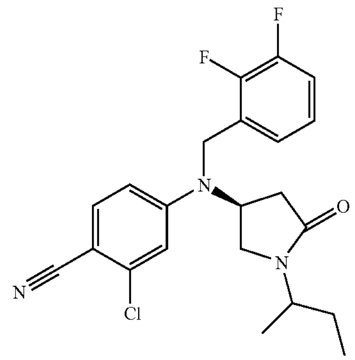 | 418.5 | 2-chloro-4-{[(2,3-difluorophenyl)methyl][(3S)-1-(1-methylpropyl)-5-oxo-3-pyrrolidinyl]amino}benzonitrile |
| 78 | 6 | 2 | 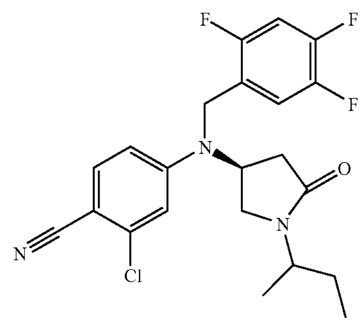 | 436.5 | 2-chloro-4-{[(3S)-1-(1-methylpropyl)-5-oxo-3-pyrrolidinyl][(2,4,5-trifluorophenyl)methyl]amino}benzonitrile |
| 79 | 6 | 2 | 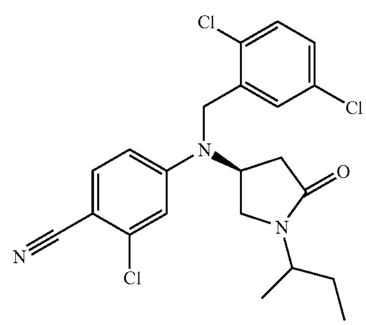 | 452.3 | 2-chloro-4-{[(2,5-dichlorophenyl)methyl][(3S)-1-(1-methylpropyl)-5-oxo-3-pyrrolidinyl]amino}benzonitrile |
| 80 | 6 | 2 | 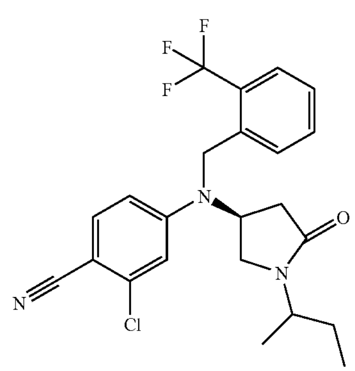 | 450.3 | 2-chloro-4-([[(3S)-1-(1-methylpropyl)-5-oxo-3-pyrrolidinyl]{[2-(trifluoromethyl)phenyl]methyl}amino)benzonitrile |

| Ex # | Int | Proced. | Structure | m/z | Name |
|------|-----|---------|-----------|-----|------|
| 81 | 6 | 2 | 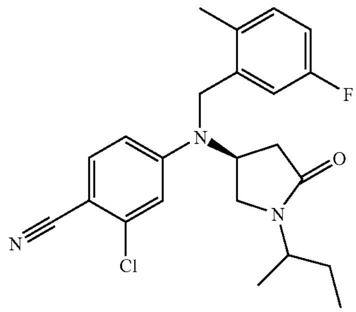 | 414.5 | 2-chloro-4-{[(5-fluoro-2-methylphenyl)methyl][(3S)-1-(1-methylpropyl)-5-oxo-3-pyrrolidinyl]amino}benzonitrile |
| 82 | 6 | 2 | 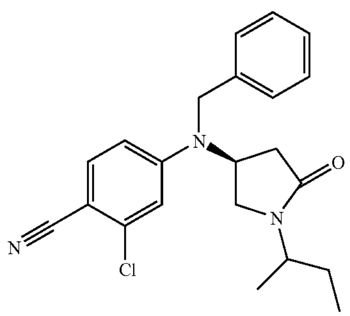 | 382.4 | 2-chloro-4-[[(3S)-1-(1-methylpropyl)-5-oxo-3-pyrrolidinyl](phenylmethyl)amino]benzonitrile |
| 83 | 7 | 2 | 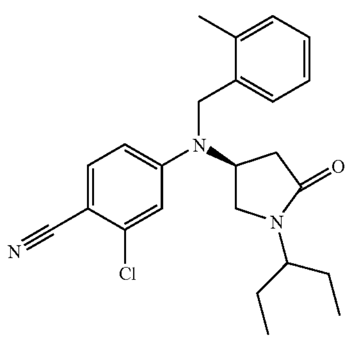 | 410.5 | 2-chloro-4-{[(3S)-1-(1-ethylpropyl)-5-oxo-3-pyrrolidinyl][(2-methylphenyl)methyl]amino}benzonitrile |
| 84 | 7 | 2 | 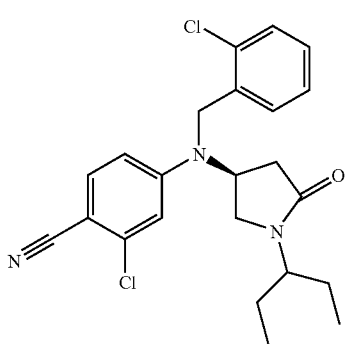 | 430.4 | 2-chloro-4-{[(2-chlorophenyl)methyl][(3S)-1-(1-ethylpropyl)-5-oxo-3-pyrrolidinyl]amino}benzonitrile |

-continued

| Ex # | Int | Proced. | Structure | m/z | Name |
|---|---|---|---|---|---|
| 85 | 7 | 2 | 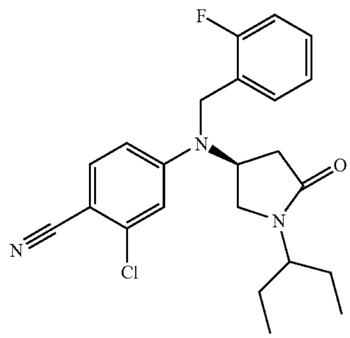 | 414.5 | 2-chloro-4-{[(3S)-1-(1-ethylpropyl)-5-oxo-3-pyrrolidinyl][(2-fluorophenyl)methyl]amino}benzonitrile |
| 86 | 7 | 2 | 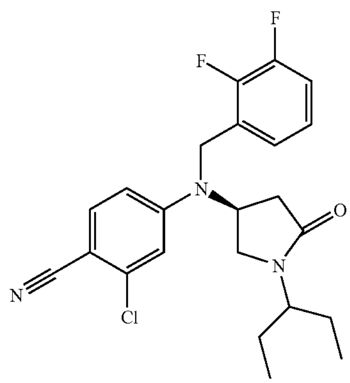 | 432.5 | 2-chloro-4-{[(2,3-difluorophenyl)methyl][(3S)-1-(1-ethylpropyl)-5-oxo-3-pyrrolidinyl]amino}benzonitrile |
| 87 | 7 | 2 | 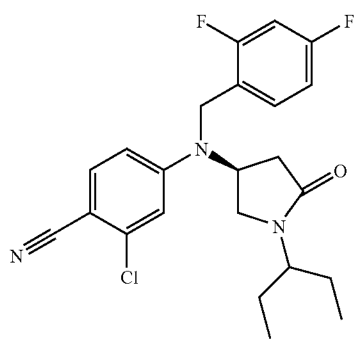 | 432.5 | 2-chloro-4-{[(2,4-difluorophenyl)methyl][(3S)-1-(1-ethylpropyl)-5-oxo-3-pyrrolidinyl]amino}benzonitrile |
| 88 | 7 | 2 | 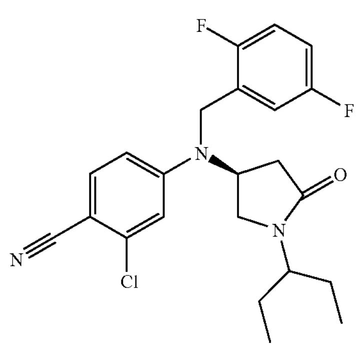 | 432.5 | 2-chloro-4-{[(2,5-difluorophenyl)methyl][(3S)-1-(1-ethylpropyl)-5-oxo-3-pyrrolidinyl]amino}benzonitrile |

| Ex # | Int | Proced. | Structure | m/z | Name |
|---|---|---|---|---|---|
| 89 | 7 | 2 | 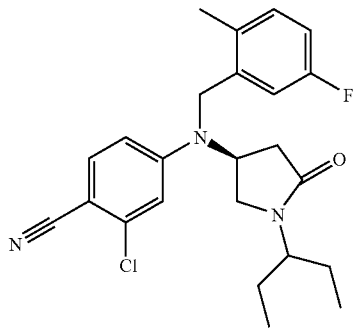 | 428.3 | 2-chloro-4-{[(3S)-1-(1-ethylpropyl)-5-oxo-3-pyrrolidinyl][(5-fluoro-2-methylphenyl)methyl]amino}benzonitrile |
| 90 | 7 | 2 | 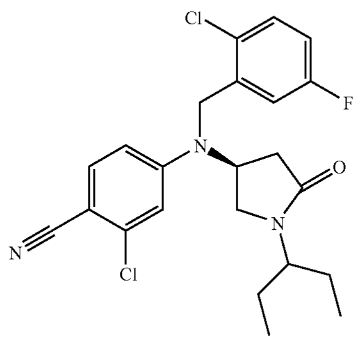 | 448.4 | 2-chloro-4-{[(2-chloro-5-fluorophenyl)methyl][(3S)-1-(1-ethylpropyl)-5-oxo-3-pyrrolidinyl]amino}benzonitrile |
| 91 | 7 | 2 | 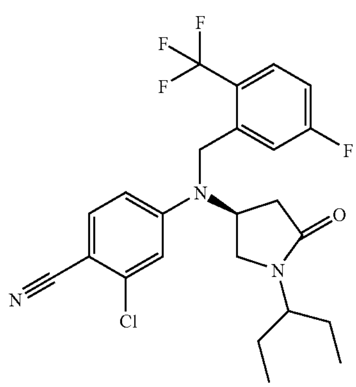 | 482.3 | 2-chloro-4-([(3S)-1-(1-ethylpropyl)-5-oxo-3-pyrrolidinyl]{[5-fluoro-2-(trifluoromethyl)phenyl]methyl}amino)benzonitrile |
| 92 | 7 | 2 | 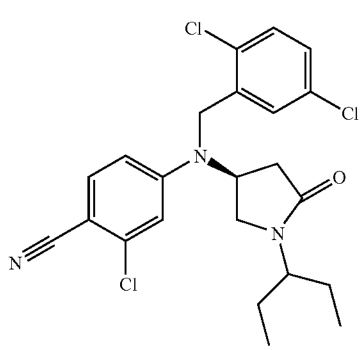 | 463.8 | 2-chloro-4-{[(2,5-dichlorophenyl)methyl][(3S)-1-(1-ethylpropyl)-5-oxo-3-pyrrolidinyl]amino}benzonitrile |

| Ex # | Int | Proced. | Structure | m/z | Name |
|---|---|---|---|---|---|
| 93 | 7 | 2 | 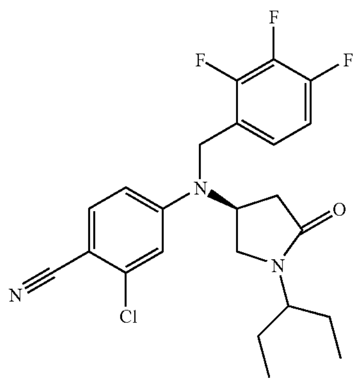 | 449.6 | 2-chloro-4-{[(3S)-1-(1-ethylpropyl)-5-oxo-3-pyrrolidinyl][(2,3,4-trifluorophenyl)methyl]amino}benzonitrile |
| 94 | 7 | 2 | 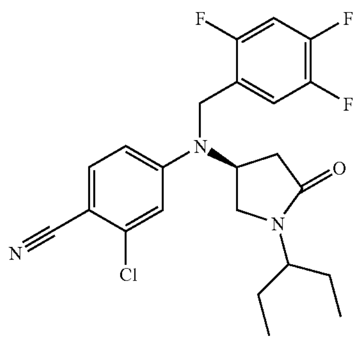 | 449.8 | 2-chloro-4-{[(3S)-1-(1-ethylpropyl)-5-oxo-3-pyrrolidinyl][(2,4,5-trifluorophenyl)methyl]amino}benzonitrile |
| 95 | 8 | 2 | 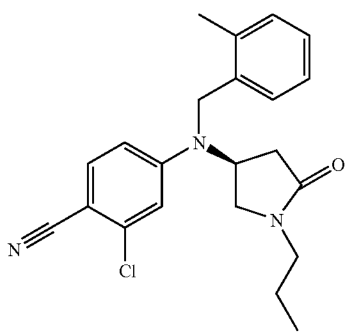 | 382.7 | 2-chloro-4-{[(2-methylphenyl)methyl][(3S)-5-oxo-1-propyl-3-pyrrolidinyl]amino}benzonitrile |
| 96 | 8 | 2 | 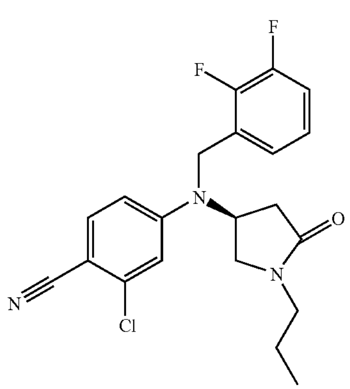 | 404.6 | 2-chloro-4-{[(2,3-difluorophenyl)methyl][(3S)-5-oxo-1-propyl-3-pyrrolidinyl]amino}benzonitrile |

-continued

| Ex # | Int | Proced. | Structure | m/z | Name |
|---|---|---|---|---|---|
| 97 | 8 | 2 | 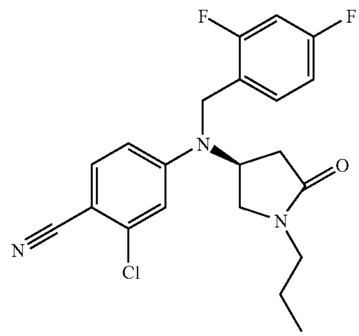 | 404.6 | 2-chloro-4-{[(2,4-difluorophenyl)methyl][(3S)-5-oxo-1-propyl-3-pyrrolidinyl]amino}benzonitrile |
| 98 | 8 | 2 | 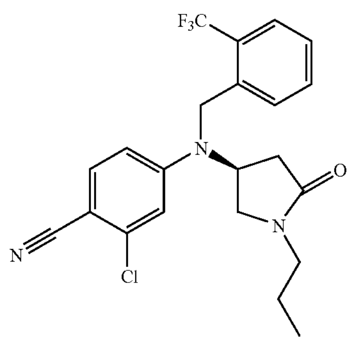 | 435.9 | 2-chloro-4-([(3S)-5-oxo-1-propyl-3-pyrrolidinyl]{[2-(trifluoromethyl)phenyl]methyl}amino)benzonitrile |
| 99 | 8 | 2 | 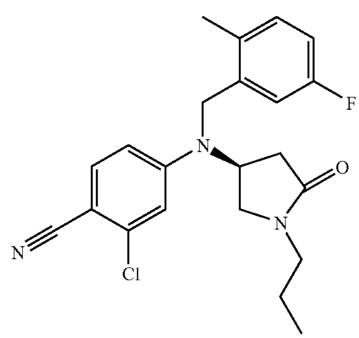 | 400.2 | 2-chloro-4-{[(5-fluoro-2-methylphenyl)methyl][(3S)-5-oxo-1-propyl-3-pyrrolidinyl]amino}benzonitrile |
| 100 | 8 | 2 | 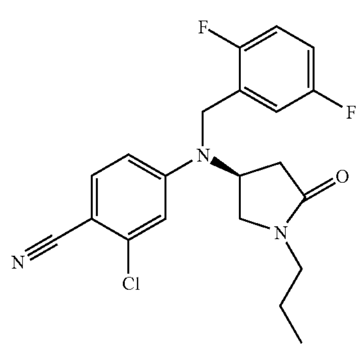 | 404.6 | 2-chloro-4-{[(2,5-difluorophenyl)methyl][(3S)-5-oxo-1-propyl-3-pyrrolidinyl]amino}benzonitrile |

-continued

| Ex # | Int | Proced. | Structure | m/z | Name |
|---|---|---|---|---|---|
| 101 | 9 | 2 | 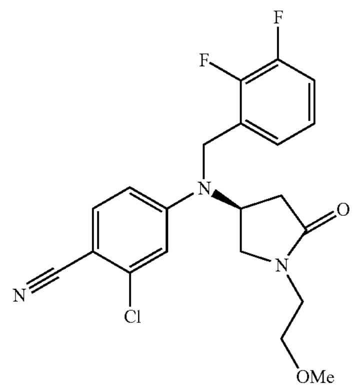 | 420.3 | 2-chloro-4-([[(2,3-difluorophenyl)methyl]{(3S)-1-[2-(methyloxy)ethyl]-5-oxo-3-pyrrolidinyl}amino)benzonitrile |
| 102 | 9 | 2 | 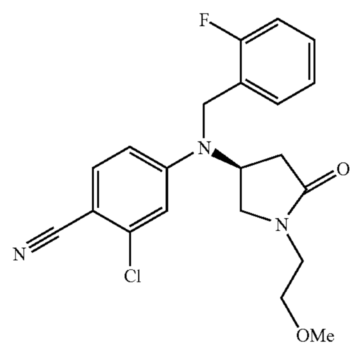 | 402.7 | 2-chloro-4-([[(2-fluorophenyl)methyl]{(3S)-1-[2-(methyloxy)ethyl]-5-oxo-3-pyrrolidinyl}amino)benzonitrile |
| 103 | 9 | 2 | 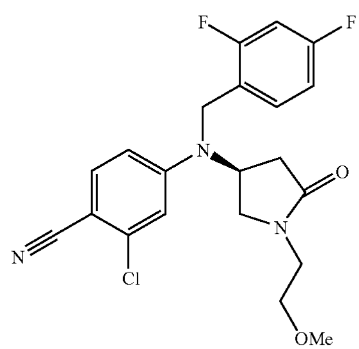 | 420.3 | 2-chloro-4-([[(2,4-difluorophenyl)methyl]{(3S)-1-[2-(methyloxy)ethyl]-5-oxo-3-pyrrolidinyl}amino)benzonitrile |
| 104 | 9 | 2 | 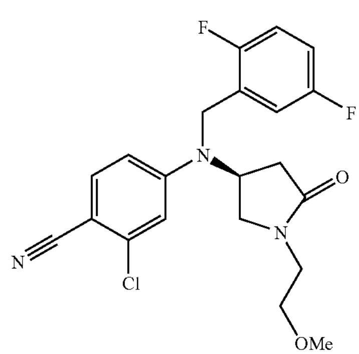 | 420.3 | 2-chloro-4-([[(2,5-difluorophenyl)methyl]{(3S)-1-[2-(methyloxy)ethyl]-5-oxo-3-pyrrolidinyl}amino)benzonitrile |

| Ex # | Int | Proced. | Structure | m/z | Name |
|---|---|---|---|---|---|
| 105 | 9 | 2 | 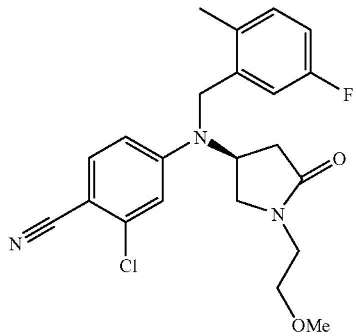 | 416.2 | 2-chloro-4-([[(5-fluoro-2-methylphenyl)methyl]{(3S)-1-[2-(methyloxy)ethyl]-5-oxo-3-pyrrolidinyl}amino)benzonitrile |
| 106 | 9 | 2 | 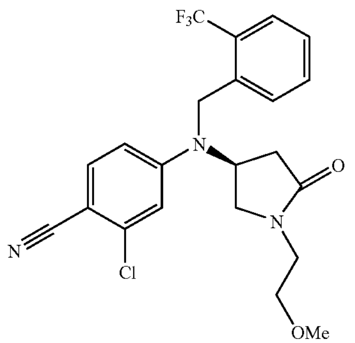 | 452.1 | 2-chloro-4-({(3S)-1-[2-(methyloxy)ethyl]-5-oxo-3-pyrrolidinyl}{[2-(trifluoromethyl)phenyl]methyl}amino)benzonitrile |

The invention claimed is:

1. A compound which is 2-chloro-4-{[(3S)-1-methyl-5-oxo-3-pyrrolidinyl][(2-methylphenyl)methyl]amino}benzonitrile.

2. A composition that comprises a) the compound of claim 1; and b) a pharmaceutically acceptable carrier.

3. A pharmaceutically acceptable salt of the compound of claim 1.

4. A method comprising administering to a patient in need thereof an effective amount of the compound of claim 1 or a pharmaceutically-acceptable salt thereof to treat endometreosis, uterine fibroids, dysmenorrhea, menorrhagia, pre-term labor, or infertility.

5. A method comprising administering to a patient in need thereof an effective amount of the compound of claim 1 or a pharmaceutically-acceptable salt thereof to provide contraception or hormone therapy.

* * * * *